United States Patent [19]

Sakai et al.

[11] 4,064,351
[45] Dec. 20, 1977

[54] 9-OXO-15 ξ-HYDROXY-20-ALKYLIDENE-PROST-13(TRANS)-ENOIC ACID DERIVATIVES

[75] Inventors: Kiyoshi Sakai; Koichi Kojima; Junya Ide; Shinsaku Kobayashi, all of Tokyo, Japan

[73] Assignee: Sankyo Company Limited, Tokyo, Japan

[21] Appl. No.: 753,277

[22] Filed: Dec. 22, 1976

Related U.S. Application Data

[63] Continuation of Ser. No. 611,306, Sept. 8, 1975, abandoned.

[30] Foreign Application Priority Data

Sept. 19, 1974 Japan .................. 49-108143
May 21, 1975 Japan .................. 50-60520

[51] Int. Cl.$^2$ .......................... C07C 177/00
[52] U.S. Cl. .................. 560/121; 260/327 M; 260/343.3 R; 260/343.3 P; 260/345.8 P; 260/346.2 L; 260/514 D; 542/426; 424/305; 424/317
[58] Field of Search .............. 260/408 D, 514 D

[56] References Cited

U.S. PATENT DOCUMENTS 3,919,285  11/1975  Axen .................. 260/468

Primary Examiner—Robert Gerstl
Attorney, Agent, or Firm—Flynn & Frishauf

[57] ABSTRACT

Prostanoic acid derivatives having the formula

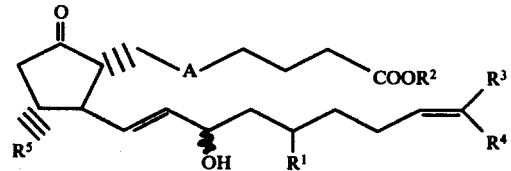

wherein A represents ethylene group or cis-vinylene group, $R^1$ and $R^2$ may be the same or different and each represents hydrogen atom or an alkyl group having 1-3 carbon atoms, $R^3$ and $R^4$ may be the same or different and each represents an alkyl group having 1-3 carbon atoms and $R^5$ represents hydrogen atom or hydroxyl group and the pharmaceutically acceptable salts thereof and a process for the preparation thereof.

The compounds are useful as anti-ulcerogenic or bronchodilating agents and may be prepared by oxidizing 9ξ-hydroxy-15ξ-protected-hydroxy-20-alkylideneprost-13(trans)-enoic acid derivatives.

8 Claims, No Drawings

9-OXO-15 ξ-HYDROXY-20-ALKYLIDENEPROST-13(TRANS)-ENOIC ACID DERIVATIVES

This is a continuation, of application Ser. No. 611,306, filed Sept. 8, 1975 now abandoned.

This invention relates to a novel prostaglandin derivative and a novel process for the preparation thereof.

More particularly, it relates to a prostaglandin derivative having the formula

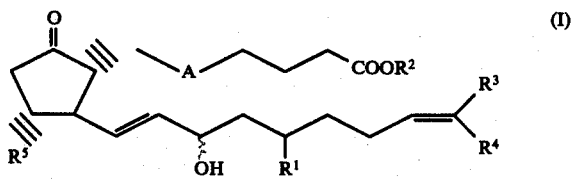

wherein A represents ethylene group or cis-vinylene group, $R^1$ and $R^2$ may be the same or different and each represents hydrogen atom or an alkyl group having 1-3 carbon atoms, $R^3$ and $R^4$ may be the same or different and each represents an alkyl group having 1-3 carbon atoms and $R^5$ represents hydrogen atom or hydroxyl group and the pharmaceutically acceptable salts thereof and also relates to a process for the preparation thereof.

The prostaglandin derivatives (I) of this invention are useful as anti-ulcerogenic or bronchodilating agents.

In the above formula (I), $R^1$ and $R^2$ may be the same or different and each represents preferably hydrogen, methyl, ethyl, n-propyl or isopropyl. $R^3$ and $R^4$ may be the same or different and each represents preferably methyl, ethyl, n-propyl or isopropyl.

In the formula (I) and elsewhere in this specification, a bond attached to the cyclopentane nucleus which is in the α-configuration, i.e., extends below the plane of the cyclopentane ring, is represented by a dotted line, and a bond which is in the β-configuration, i.e., extends above the plane of the cyclopentane ring, is represented by a solid line. The wavy line indicates that either steric configuration is possible.

The compounds of the aforementioned general formula (I) in which $R^2$ is hydrogen atom may be converted into pharmaceutically acceptable salts by conventional means. The pharmaceutically acceptable salt may be exemplified by a salt of an alkali or alkaline earth metal such as sodium, potassium, magnesium and calcium, an ammonium salt, a quarternary ammonium salt such as a salt of tetramethylammonium, tetraethylammonium, benzyltrimethylammonium and phenyltriethylammonium, a salt of a lower aliphatic, alicyclic or aromatic-aliphatic amine such as methylamine, ethylamine, dimethylamine, diethylamine, trimethylamine, triethylamine, N-methylhexylamine, cyclopentylamine, dicyclohexylamine, benzylamine, dibenzylamine, α-phenylethylamine and ethylenediamine, a salt of a heterocyclic amine or a lower alkyl derivative thereof such as piperidine, morpholine, pyrrolidine, piperazine, pyridine, 1-methylpiperazine and 4-ethylmorpholine, and a salt of an amine containing hydrophilic groups such as monoethanolamine, ethyldiethanolamine and 2-amino-1-butanol.

The prostaglandin derivatives having the aforementioned general formula (I) are novel compounds which have not been shown in previous publications.

As a result of our research, we have found that the present prostaglandin derivatives (I) show prominent inhibitory activity of gastric secretion and bronchodilating activity and, on the other hand, no or little hypotensive and intestinal tube-contracting activity.

The inhibitory activity of gastric secretion and bronchodilating activity of the present prostaglandin derivatives (I) will be evident from the following pharmacological comparative test data.

1. Inhibition of gastric secretion

Method

The method employed was essentially same as described by M. N. Ghosh and H. O. Schild in British Journal of Pharmacology and Chemotherapy, vol. 13, 54-61 (1958).

Through the stomach of a male rat (Donryu strain) anesthetized by administration of urethane was perfused a physiological saline solution containing a small amount of sodium hydroxide at a rate of 1 ml/min. Then 10 μg/kg/hr of a gastric secretion stimulating agent, tetragastrine, was continuously injected into the vein of said rat until pH of the outflowing perfusate reached approximately 3 and said value remained. Thereupon, a certain amount of the test compounds was administered at a certain rate into the vein for 30 minutes, and pH of the outflowing perfusate was measured. The measurement was repeated with variation of the administering amount.

Result

Table 1 shows the amounts needed to increase the pH by 1.0 by the intravenous administration.

Table 1

| Drug | Dose (mg/kg/hr) |
| --- | --- |
| Compound A | 0.074 |
| Compound B | 0.070 |
| $PGE_1$ | 0.086 |

Compound A: 9-Oxo-11α, 15α-dihydroxy-17β-methyl-20-isopropylideneprost-13(trans)-enoic acid.
Compound B: 9-Oxo-11α, 15α-dihydroxy-17β-methyl-20-isopropylideneprost-5-(cis),13(trans)-dienoic acid.

The compounds A and B are, as shown above, similar to or higher than prostaglandin $E_1(PGE_1)$ in an inhibition of gastric secretion. According to our further investigations, the present compounds (I) are only about one twohundredth as strong as prostaglandin $E_1$ in uterus contraction. That is to say, the present compounds have characteristics which cannot be seen in the natural prostaglandins.

2. Bronchodilating activity

Method

The test compounds were administered through intravenous injection to a guinea pig (body weight: 400 – 600 g) anesthetized by administration of sodium pentobarbital, and 2 – 3 μg/kg of histamine was administered through intravenous injection. Inhibitory ratio of increase in air-way resistance was determined by the variant method of Konzett-Rossler method [Archiv fur Experimentelle Pathologie und Pharmakologie, vol. 195, 71 (1940)].

Result

The tested prostaglandins exhibited bronchodilating activity in guinea pigs. Table 2 shows the results.

Table 2

| Drug | 50% Inhibition Dose ($ID_{50}$) of increase of air-way resistance in guinea pigs $ID_{50}$ (γ/kg. i.r.) |
|---|---|
| Compound A | 0.019 (0.026 – 0.015)* |
| Compound B | 0.014 (0.019 – 0.010) |
| Compound C | 0.032 (0.048 – 0.022) |
| Compound D | 0.021 (0.035 – 0.013) |
| Compound E | 0.039 (0.056 – 0.028) |
| $PGE_1$ | 0.14 (0.19 – 0.11) |
| $PGE_2$ | 0.21 (0.28 – 0.16) |
| Isoproterenol | 0.08 (0.14 – 0.05) |
| Salbutanol | 0.042 (0.058 – 0.031) |
| Compound A : | the same as above |
| Compound B : | the same as above |
| Compound C : | 9-Oxo-15α-hydroxy-20-isopropylideneprost-13(trans)-enoic acid |
| Compound D : | 9-Oxo-15α-hydroxy-20-isopropylideneprost-5(cis),13-(trans)-dienoic acid |
| Compound E : | 9-Oxo-11α,15α-dihydroxy-20-isopropylideneprost-5(cis), 13(trans)-dienoic acid |

*95% confidence limit.

As a result of our investigations, it is found that the bronchodilating activity of the present compound (I) is not inhibited by a β-adrenergic blocking agent, which inhibits an activity of sulbutamol and isoproterenol.

Accordingly, the compounds having the aforementioned general formula (I) are of value as medicines used for either inhibition of gastric secretion or bronchodilation. As the administration procedure for the former use, there may be mentioned parenteral administration such as intravenous, subcutaneous and intramuscular injections and oral administration by the use of tablets, granules, capsules and the like. The dosage to be administered may vary dependent upon condition, age, body weight, administration procedure and the like, and may generally be within about 0.1 mg to 15 mg per day for an adult. For the administration for the latter use, an aerosol spray may ordinarily be employed. The dosage to be administered may vary dependent upon condition, age, body weight and the like, and may ordinarily be within 20 μg to 150 μg per day for an adult.

Representative examples of the compound of the aforementioned general formula (I) are set out below. However, compounds of this invention are not limited thereto.

1. 9-Oxo-11α,15α(or β)-dihydroxy-20-isopropylideneprost-13(trans)-enoic acid, and methyl, ethyl, n-propyl and isopropyl esters of the same
2. 9-Oxo-11α,15α(or β)-dihydroxy-20-isopropylideneprost-5(cis),13(trans)-dienoic acid, and methyl, ethyl, n-propyl and isopropyl esters of the same
3. 9-Oxo-11α,15α(or β)-dihydroxy-17β-methyl-20-isopropylideneprost-13(trans)-enoic acid, and methyl, ethyl, n-propyl and isopropyl esters of the same
4. 9-Oxo-11α,15α(or β)-dihydroxy-17β-methyl-20-isopropylideneprost-5(cis),13(trans)-dienoic acid, and methyl, ethyl, n-propyl and isopropyl esters of the same
5. 9-Oxo-11α,15α/(or β)-dihydroxy-17β-methyl-20-(1'-methyl)-isopropylideneprost-13(trans)-enoic acid, and methyl, ethyl, n-propyl and isopropyl esters of the same
6. 9-Oxo-11α,15α/(or β)-dihydroxy-17β-methyl-20-(1'-methyl)-isopropylideneprost-5(cis),13(trans)-dienoic acid, and methyl, ethyl, n-propyl and isopropyl esters of the same
7. 9-Oxo-11α,15α/(or β)-dihydroxy-17β-methyl-20-(1',3'-dimethyl)-isopropylideneprost-13(trans)-enoic acid, and methyl, ethyl, n-propyl and isopropyl esters of the same
8. 9-Oxo-11α,15α/(or β)-dihydroxy-17β-methyl-20-(1',3'-dimethyl)-isopropylideneprost-5(cis),13(trans)-dienoic acid, and methyl, ethyl, n-propyl and isopropyl esters of the same
9. 9-Oxo-11α 15α(or β)-dihydroxy-20-(1'-methyl)-isopropylideneprost-13(trans)-enoic acid, and methyl, ethyl, n-propyl and isopropyl esters of the same
10. 9-Oxo-11α,15α(or β)-dihydroxy-20-(1'-methyl)-isopropylideneprost-5(cis),13(trans)-dienoic acid, and methyl, ethyl, n-propyl and isopropyl esters of the same
11. 9-Oxo-11α,15α(or β)-dihydroxy-20-(1',3'-dimethyl)-isopropylideneprost-13(trans)-enoic acid, and methyl, ethyl, n-propyl and isopropyl esters of the same
12. 9-Oxo-11α,15α(or β)-dihydroxy-20-(1',3'-dimethyl)isopropylideneprost-5(cis),13(trans)-dienoic acid, and methyl, ethyl, n-propyl and isopropyl esters of the same
13. 9-Oxo-15α(or β)-hydroxy-20-isopropylideneprost-13(trans)-enoic acid, and methyl, ethyl, n-propyl and isopropyl esters of the same
14. 9-Oxo-15α/(or β)-hydroxy-17β-methyl-20-isopropylideneprost-13(trans)-enoic acid, and methyl, ethyl, n-propyl and isopropyl esters of the same
15. 9-Oxo-15α(or β)-hydroxy-20-isopropylideneprost-5(cis),13(trans)-dienoic acid, and methyl, ethyl, n-propyl and isopropyl esters of the same
16. 9-Oxo-15α(or β)-hydroxy-17β-methyl-20-isopropylideneprost-5(cis),13(trans)-dienoic acid, and methyl, ethyl, n-propyl and isopropyl esters of the same According to the process of this invention, the compounds having the aforementioned general formula (I) may be obtained by oxidizing a compound having the general formula

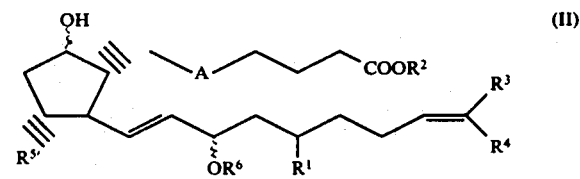
(II)

wherein A, $R^1$, $R^2$, $R^3$ and $R^4$ are the same as above, $R^{5'}$ represents hydrogen atom or a group — $OR^6$ and $R^6$ represents a protective group for hydroxyl group to prepare a compound having the general formula

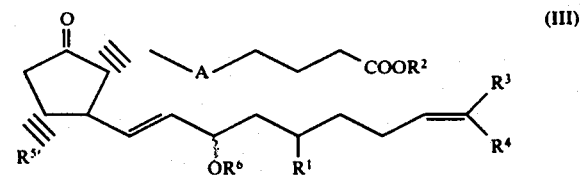
(III)

wherein A, $R^1$, $R^2$, $R^3$, $R^4$, $R^{5'}$ and $R^6$ are the same as above and removing the protective groups from the hydroxyl groups of the resulting product.

There is no specific limitation on the protective group for the hydroxyl group, so far as it does not affect another moiety of the compound during the replacement reaction of the protective group with hydrogen which shall take place afterwards. Such a protective group may be exemplified by a 5- or 6-membered cyclic group containing an oxygen or sulfur atom in its ring which may be substituted with alkoxy, for instance, 2-tetrahydrofuranyl, 2-tetrahydropyranyl, 2-tetrahydrothienyl, 2-tetrahydrothiopyranyl and 4-methoxytetrahydropyran-4-yl; a straight or branched alkyl group containing 1 – 5 carbon atoms, for instance, methyl, ethyl, n-propyl, isopropyl, n-butyl, isobutyl, n-pentyl and isopentyl; a straight or branched alkyl group containing 1 – 5 carbon atoms and carrying alkoxy as substituent, for instance, methoxymethyl, ethoxymethyl, n-propoxymethyl, isopropoxymethyl, n-butoxymethyl, isobutoxymethyl, n-pentoxymethyl, isopentoxymethyl, 1-ethoxymethyl, 1-ethoxypropyl, 2-ethoxybutyl and 1-ethoxypentyl; a straight or branched trialkylsilyl group containing 1 – 5 carbon atoms, for instance, trimethylsilyl, triethylsilyl, tri-n-propylsilyl, triisopropylsilyl, tri-n-butylsilyl, triisobutylsilyl and tri-n-pentylsilyl; and a carboxylic acid ester residue having the formula $$XOCO- \qquad (IV)$$

in which X represents a straight or branched alkyl group containing 1 – 5 carbon atoms, for instance, methyl, ethyl, n-propyl, isopropyl, n-butyl, isobutyl and n-pentyl, an ethyl group carrying 1 – 3 halogen atoms as substituent in the $\beta$-position, for instance, 2,2,2-trichloroethyl, 2,2-dibromoethyl and 2-iodoethyl, a phenyl group which may have substituents, for instance, phenyl, 4-nitrophenyl, 2-chlorophenyl and 2,4-dichlorophenyl, and an aralkyl group consisting of a substituted or unsubstituted aromatic ring and an alkylene moiety containing 1 – 5 carbon atoms for instance, benzyl, phenethyl, phenylpropyl, phenylbutyl, phenylpentyl, 4-nitrobenzyl and 4-chlorophenethyl. However, the above-mentioned protective groups are not limitative.

In the process of the present invention, the reaction for preparing a compound of the aforementioned formula (III) through oxidation of a compound of the aforementioned formula (II) is performed by the use of an oxidizing agent in the presence or absence of a solvent. An oxidizing agent employed may preferably be one of chromic acids such as chromic acid, chromic anhydride, a chromic anhydride - pyridine complex (Collins reagent), chromic anhydride - conc. sulfuric acid - water (Jones reagent), sodium dichromate and potassium dichromate; active halogenated organic compounds such as N-bromoacetamide, N-bromosuccinimide, N-bromophthalimide, N-chloro-p-toluenesulfonamide and N-chlorobenzenesulfonamide; aluminum alkoxides such as aluminum tert-butoxide and aluminum isopropoxide; dimethylsulfoxide - dicyclohexylcarbodiimide and dimethylsulfoxide - acetic anhydride. There is no specific limitation on the solvent employed in the case involving a solvent so far as it does not participate in the reaction. However, preferred solvents are as follows. In the case of employing one of the chromic acids, an organic acid or a mixture of an organic acid and an organic anhydride such as acetic acid and acetic acid - acetic anhydride or a halogenated hydrocarbon such as dichloromethane, chloroform and carbon tetrachloride is preferred. In the case of employing an active halogenated organic compound, an aqueous organic solvent such as aqueous tert-butanol, aqueous acetone and aqueous pyridine is preferred. In the case of employing an aluminum alkoxide, an aromatic hydrocarbon such as benzene, toluene and xylene is preferred. In the case of employing either dimethylsulfoxide - dicyclohexylcarbodiimide or dimethylsulfoxide - acetic anhydride, ordinarily, another solvent is not specifically necessary if an excess amount of dimethylsulfoxide is employed. In the case of employing an aluminum alkoxide, it is preferable to use as a hydrogen - acceptor an excess amount of ketone such as acetone, methyl ethyl ketone, cyclohexanone and benzoquinone in addition to the above-mentioned solvent. In this reaction, water must be removed completely from the reaction system. In the case of employing dimethyl-sulfoxide - dicyclohexylcarbodiimide, a catalytic amount of an acid such as phosphoric acid and acetic acid is employed in the usual manner. In the present reaction, one of the chromic acids, especially, a chromic anhydride - pyridine complex (Collins reagent) or chromic anhydride - conc. sulfuric acid - water (Jones reagent) is ordinarily employed as the most preferred oxidizing agent. There is no specific limitation on the reaction temperature, but a relatively lower temperature is preferably adopted so as to avoid side-reactions. It may usually be in a range of $-20°$ C to room temperature, and the most preferred is in a range of 0° C to room temperature. The reaction period varies dependent mainly upon the reaction temperature and the kind of an oxidizing agent used, but it may be in a range of about 5 minutes to two hours.

After completion of the reaction, the desired compound of the oxidation reaction is taken out of the reaction mixture in the usual way. For instance, after completion of the reaction, an organic solvent such as ether is added to the reaction mixture and insoluble materials are filtered off. The resulting organic solvent portion is washed and dried, and then a solvent is distilled off from the organic solvent layer to give the desired compound. The desired compound thus obtained may be further purified in the usual way, for example, with column chromatography or thin-layer chromatography, if necessary.

The reaction for removing the protective group from the hydroxyl group of the compound of the aforementioned general formula (III) which is thus obtained is dependent upon the kind of a protective group. In case the protective group for the hydroxyl group is, for example, a heterocyclic group such as 2-tetrahydropyranyl, an alkyl group carrying substituents of alkoxy such as methoxymethyl and a cycloalkyl group carrying substituents of alkoxy such as 1-methoxycyclohexyl, the reaction is easily carried out by bringing the compound into contact with an acid. An acid employed may preferably be an organic acid such as formic acid, acetic acid, propionic acid, butyric acid, oxalic acid and malonic acid or a mineral acid such as hydrochloric acid, hydrobromic acid and sulfuric acid. The reaction may be carried out in the presence or absence of a solvent. However, a solvent is preferably employed so as to perform the reaction smoothly. There is no specific limitation on the solvent used so far as it does not participate in the reaction, and water, an alcohol such as methanol and ethanol, ether such as tetrahydrofuran and dioxane, or a mixture of such an organic solvent and water may be preferably employed. There is no specific limitation on the reaction temperature, and the reaction may be carried out at a temperature ranging from room temperature to the reflux temperature of the solvent. The reaction is most preferably performed at room temperature. In case the protective group for the hydroxyl group is an alkyl group such as methyl, the reaction is easily performed by bringing the compound into contact with a boron halide such as boron trichloride and boron tribromide.

The reaction may be carried out in the presence or absence of a solvent. However, a solvent is preferably employed so as to carry out the reaction smoothly. There is no specific limitation on the solvent used so far as it does not participate in the reaction, and the solvent may be preferably exemplified by a halogenated hydrocarbon, for instance, dichloromethane and chloroform. There is likewise no specific limitation on the reaction temperature, but a relatively lower temperature is preferably adopted so as to avoid side-reactions. The preferred temperature ranges from $-30°$ C to room temperature.

In case the protective group for the hydroxyl group is, for instance, a trialkylsilyl group such as trimethylsilyl, the reaction may be readily performed by bringing the compound into contact with water or water containing either an acid or a base. As an acid and a base which is contained in water, an organic acid such as formic acid, acetic acid, propionic acid, butyric acid, oxalic acid and malonic acid or a mineral acid such as hydrochloric acid, hydrobromic acid and sulfuric acid, and a hydroxide of an alkali or alkaline earth metal such as potassium hydroxide and calcium hydroxide or a carbonate of an alkali or alkaline earth metal such as potassium hydroxide and calcium hydroxide or a carbonate of an alkali or alkaline earth metal such as potassium carbonate and calcium carbonate are employed without specific limitation. If water is employed as a solvent, another solvent is not specifically needed. The other solvent may be a mixture of water and an organic solvent such as an ether, e.g., tetrahydrofuran and dioxane and an alcohol, e.g. methanol and ethanol. There is likewise no specific limitation on the reaction temperature, but, ordinarily, the reaction is preferably carried out at room temperature.

In case the protective group for the hydroxyl group is either a carbonic acid residue of an ester such as ethoxycarbonyl, the reaction may be readily performed by bringing the compound into contact with an acid or a base. An acid and a base to be employed is preferably exemplified by a mineral acid such as hydrochloric acid, hydrobromic acid and sulfuric acid and a hydroxide of an alkali or alkaline earth metal such as sodium hydroxide, potassium hydroxide and calcium hydroxide, and a carbonate of an alkali or alkaline earth metal such as sodium carbonate, potassium carbonate and calcium carbonate. The reaction may be preferably carried out under basic conditions. The reaction may be conducted in the presence or absence of a solvent, but a solvent is preferably employed so as to perform the reaction smoothly. There is no specific limitation on the solvent used so far as it does not participate in the reaction, and such a solvent may preferably be exemplified by water, as alcohol such as methanol and ethanol and an ether such as tetrahydrofuran and dioxane, and a mixture of water and one of these organic solvents. There is likewise no specific limitation on the reaction temperature, and the reaction may be conducted at a temperature ranging from room temperature to the reflux temperature of the solvent. The reaction period varies dependent mainly upon the kind of a protective group to be removed.

Of the compounds of the aforementioned general formula (I) which are obtained above, a compound having hydrogen as $R^2$ may be converted into its salt in a conventional manner.

In addition, the desired compound obtained above is a mixture of its various geometrical isomers and/or optical isomers, and they may be isolated or resolved in an appropriate synthetic step.

The compounds having the aforementioned general formula (II) which are used as a starting compound in the process of this invention are novel compounds, and may be prepared by the process shown in the following reaction schemes.

(1) Preparation of the starting compound having the above formula (II) wherein A is ethylene group and $R^y$ is a protected hydroxyl group

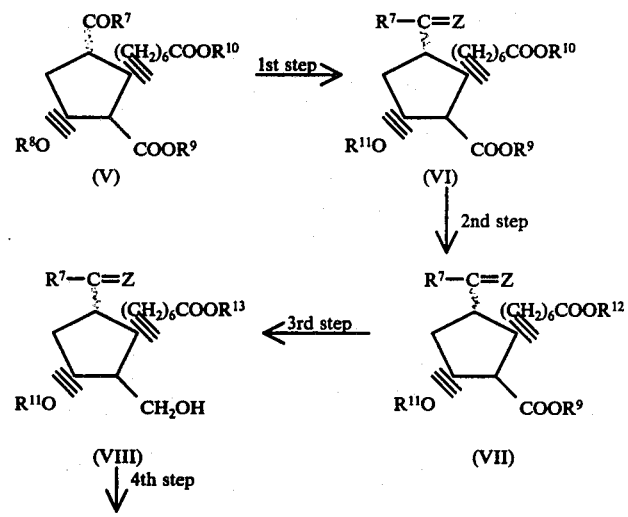

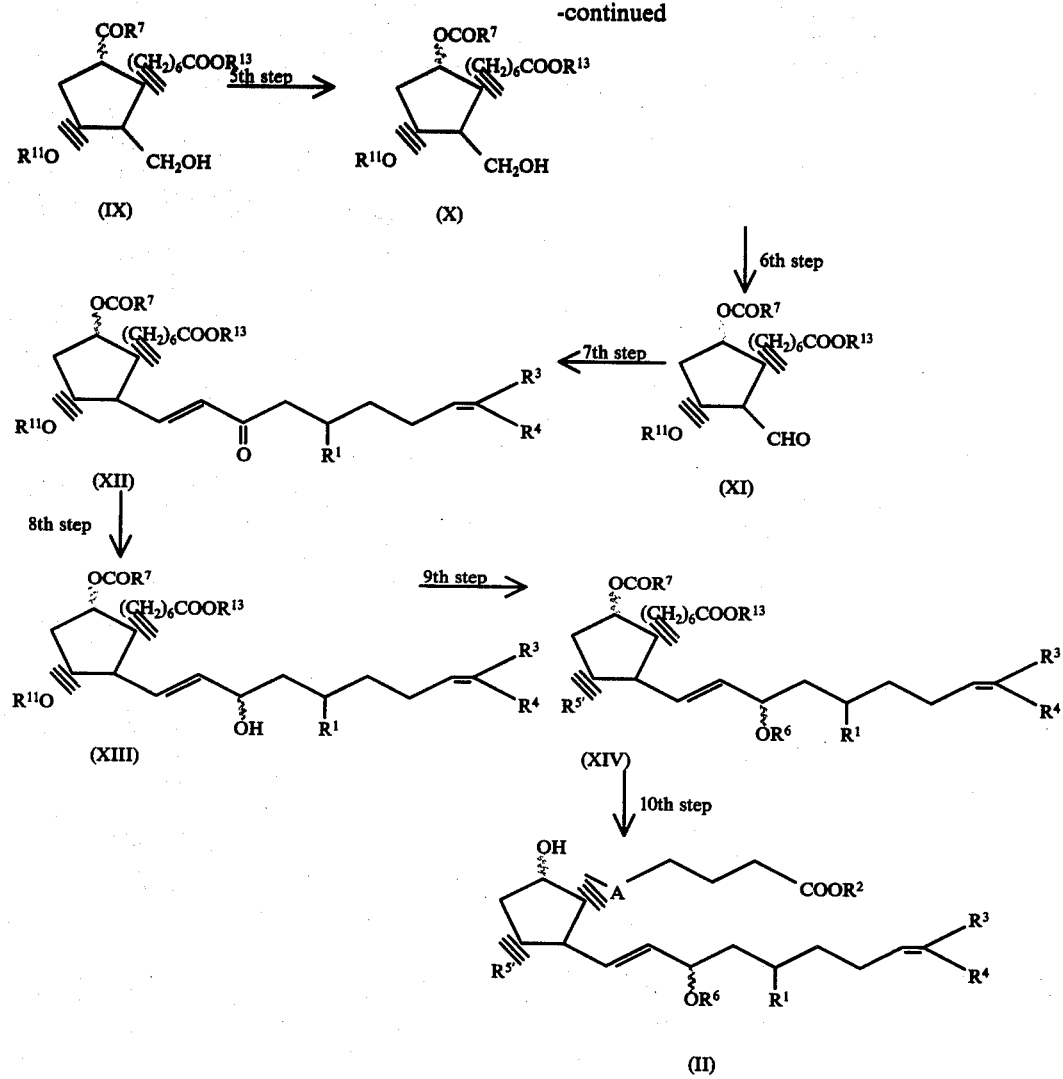

In the above formulae, A, $R^1$, $R^2$, $R^3$, $R^4$, $R^{5'}$ and $R^6$ have the same meanings as defined above.

The protective group $R^6$ for the hydroxyl group is one which cannot be removed simultaneously when $R^7CO-$, the protective group, for the hydroxyl group is removed. $R^7$ represents a straight or branched alkyl group, for instance, methyl, ethyl, n-propyl, isopropyl, n-butyl, isobutyl, tert-butyl and n-pentyl. $R^8$ and $R^{11}$ represent protective groups for the hydroxy groups. There is no specific limitation on the protective group for the hydroxyl group so far as it does not affect other moieties while said protective group shall be later on replaced with a hydrogen atom. Such a protective group may be exemplified by the protective groups as stated hereinbefore for $R^5$. $R^9$ represents a straight or branched alkyl group, for instance, methyl, ethyl, n-propyl and isopropyl. $R^{10}$ and $R^{13}$ represent protective groups for the carboxyl groups. There is no specific limitation on the protective group for the carboxyl group so far as it does not affect other moieties while said protective group shall be later on replaced with a hydrogen atom. Such a protective group may be exemplified by a hydrocarbon group, for instance, methyl, ethyl, n-propyl, isopropyl, n-butyl, isobutyl, phenyl and benzyl, a halogenated alkyl group, for instance, 2,2,2-trichloroethyl; and a heterocyclic group, for instance, 2-tetrahydropyranyl, 2-tetrahydrothiopyranyl, 2-tetrahydrofuranyl and 4-methoxytetrahydropyran-4-yl. However, the above-mentioned protective groups are not limitative. $R^{12}$ is a hydrogen atom or a group as exemplified before in the protective group for the carboxyl group. Z represents a protective group for the carboxyl group. There is no specific limitation on the protective group for the carbonyl group so far as it does not affect other moieties of the compound while the protective group shall be later on removed. Such a protective group may be exemplified by a hydroxyimino group forming oxime, a dialkoxy group such as dimethoxy and diethoxy, an alkylenedioxy group such as methylenedioxy and ethylenedioxy, and an alkylenedithio group such as trimethylenedithio. However, these protective groups are not limitative.

Each step will be explained below, by referring as the starting compound to the known compound of the general formula (V) stated in Japanese Provisional Patent Publication No. 57958/73.

The first step is directed to the preparation of a compound having the aforementioned general formula (VI), and can be performed by protecting the carbonyl group of the compound of the aforementioned general formula (V) and, if necessary, substituting the protective group for the hydroxyl group.

The order of the above-mentioned protection reaction and substitution reaction may be changeable. The reaction for protecting the carbonyl group of the compound having the aforementioned general formula (V) is performed by bringing said compound into contact with a compound capable of forming a protective group for the carbonyl in the presence or absence of a solvent. The compound used for forming a protecting group for the carbonyl group may preferably be exemplified by a hydroxylamine forming oxime such as hydroxylamine, methylhydroxylamine and sodium hydroxylaminesulfonate, an orthoformic acid ester forming ketal such as orthoformic acid methylester and orthoformic acid ethylester, an alkylene glycol forming cyclic ketal such as methylene glycol and ethylene glycol and an alkylene dithioglycol forming cyclic thioketal such as ethylene dithioglycol and trimethylenethioglycol. The reaction varies with the kind of the compound used for forming the protective group for the carbonyl group.

The substitution reaction of $R^8$, the protective group for the hydroxyl group of the compound having the aforementioned general formula (V), may be performed by removing the protective group $R^8$ from the hydroxyl group and bringing said compound into contact with a compound capable of forming a preferred protective group.

The second step is directed to the preparation of a compound having the aforementioned general formula (VII), and involves a reaction, which is conducted if necessary, for removing $R^{10}$, the protective group, from the carboxyl group of a compound having the aforementioned general formula (VI). The present reaction may be conducted as occasion arises. In the following third step (reduction reaction), a higher yield will be obtained, in case $R^{10}$, the protective group for the carboxyl group, is removed in advance of the reduction. The reaction varies with the kind of a protective group for the carboxyl group.

The third step is directed to the preparation of a compound having the aforementioned general formula (VIII), and can be performed by reducing a compound of the aforementioned general formula (VII) and then, if necessary where $R^{12}$ is a hydrogen atom, protecting the carboxyl group. The reduction is ordinarily conducted by the use of a reducing agent in the presence of a solvent.

The fourth step is directed to the preparation of a compound having the aforementioned general formula (IX), and can be performed by removing the protective group from the carbonyl group of a compound of the aforementioned general formula (VIII). The reaction for removing the protective group from the protected carbonyl group varies dependent upon the kind of the protective group.

The fifth step is directed to the preparation of a compound having the aforementioned general formula (X), and can be performed by oxidizing a compound of the aforementioned general formula (IX). The present reaction may be carried out by bringing the compound into contact with a peroxide in the presence or absence of a solvent. The peroxide employed preferably is an organic peracid such as performic acid, peracetic acid, perpropionic acid, perlauric acid, percamphoric acid, trifluoroperacetic acid, perbenzoic acid, m-chloroperbenzoic acid and monoperphthalic acid, or hydrogen peroxide. The reaction may be carried out in the presence or absence of a solvent.

The sixth step is directed to the preparation of a compound having the aforementioned general formula (XI), and can be performed by oxidizing a compound of the aforementioned general formula (X). The reaction is carried out in the presence of an oxidizing agent. Both the kind of an oxidizing agent employed and the reaction conditions are the same as those stated in the aforementioned description for the reaction for the preparation of a compound having the aforementioned general formula (III) by oxidizing a compound of the aforementioned general formula (II).

The seventh step is directed to the preparation of a compound having the aforementioned general formula (XII), and can be performed by reacting a compound of the aforementioned general formula (XI) with a Wittig reagent of the general formula

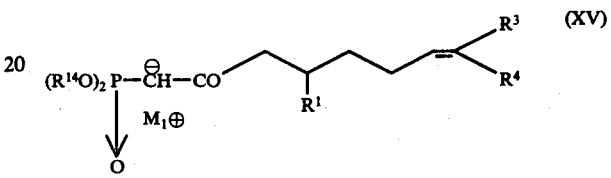

in which $R^1$, $R^3$ and $R^4$ have the same meanings as defind hereinbefore, $R^{14}$ represents an alkyl group such as methyl or an aryl group such as phenyl, and $M_1^+$ represents an metal ion such as sodium, potassium and lithium ions. There is no specific limitation on the solvent employed, so far as it is included in the solvents employed in the usual Wittig reactions.

The eighth step is directed to the preparation of a compound having the aforementioned general formula (XIII), and can be performed by reducing a compound of the aforementioned general formula (XII). The reaction may be carried out by employing a reducing agent in the presence or absence of a solvent. There is no specific limitation on the reducing agent employed, so far as it can convert the carbonyl group into a hydroxyl group without reducing the double bond. Such a reducing agent preferably is a metal hydride, for instance, sodium boron hydride, potassium boron hydride, lithium boron hydride, zinc boron hydride, lithium tri-tert-butoxyaluminum hydride, lithium trimethoxyaluminum hydride, sodium cyanoboron hydride and lithium 9b-boraperhydrophenalene hydride. The present reaction may be carried out in the presence or absence of a solvent.

The ninth step is directed to the preparation of a compound having the general formula (XIV), and can be performed by changing $R^{11}$ of the protective group for the hydroxyl group of a compound of the aforementioned general formula (XIII) and protecting the hydroxyl group. There is no specific limitation on the protective group, so far as it will not be removed while removal of $R^7CO-$ of the protective group for the hydroxyl group will be carried out afterwards. The present reaction is performed by removing the protective group $R^{11}$ from the hydroxyl group and subsequently bringing the resulting compound into contact with a compound capable of forming a preferred protective group. The compound capable of forming a protective group for the hydroxyl group and the reaction conditions adopted are the same as hereinbefore stated for the first step.

The tenth step is directed to the preparation of a compound having the aforementioned general formula (II), and can be performed by removing the protective groups $R^7CO-$ and $R^{13}$ from the hydroxyl and carboxyl groups, respectively, of a compound having the aforementioned general formula (XIV) and, if necessary, esterifying the carboxyl groups. In a certain case, the reaction for removal of the protective group $R^{13}$ from the carboxyl group may not be required, after the reaction for removal of the protective group $R^7CO-$ from the hydroxyl group. That is because, in some case, the protective group $R^{13}$ may simultaneously be removed from the carboxyl group while the reaction for removal of the protective group $R^7CO-$ from the hydroxyl group is conducted.

The reaction for removing the protective group $R^7CO-$ from the hydroxyl group may easily be performed by bringing the compound into contact with either an acid or a base.

The reaction for removal of the protective group $R^{13}$ from the carboxyl group varies dependent upon the kind of the protective group.

The reaction for esterifying the carboxyl group, which is conducted if necessary, is performed by bringing the compound into contact with an esterifying agent in the presence or absence of a solvent. There is no specific limitation on the esterifying agent employed, so far as it is included in the esterifying agents that are used in the reaction for converting a carboxyl group into an alkoxycarbonyl group.

(2) Preparation of the starting compound having the above formula (II) wherein A is cis-vinylene group and $R^9$ is a protected hydroxyl group

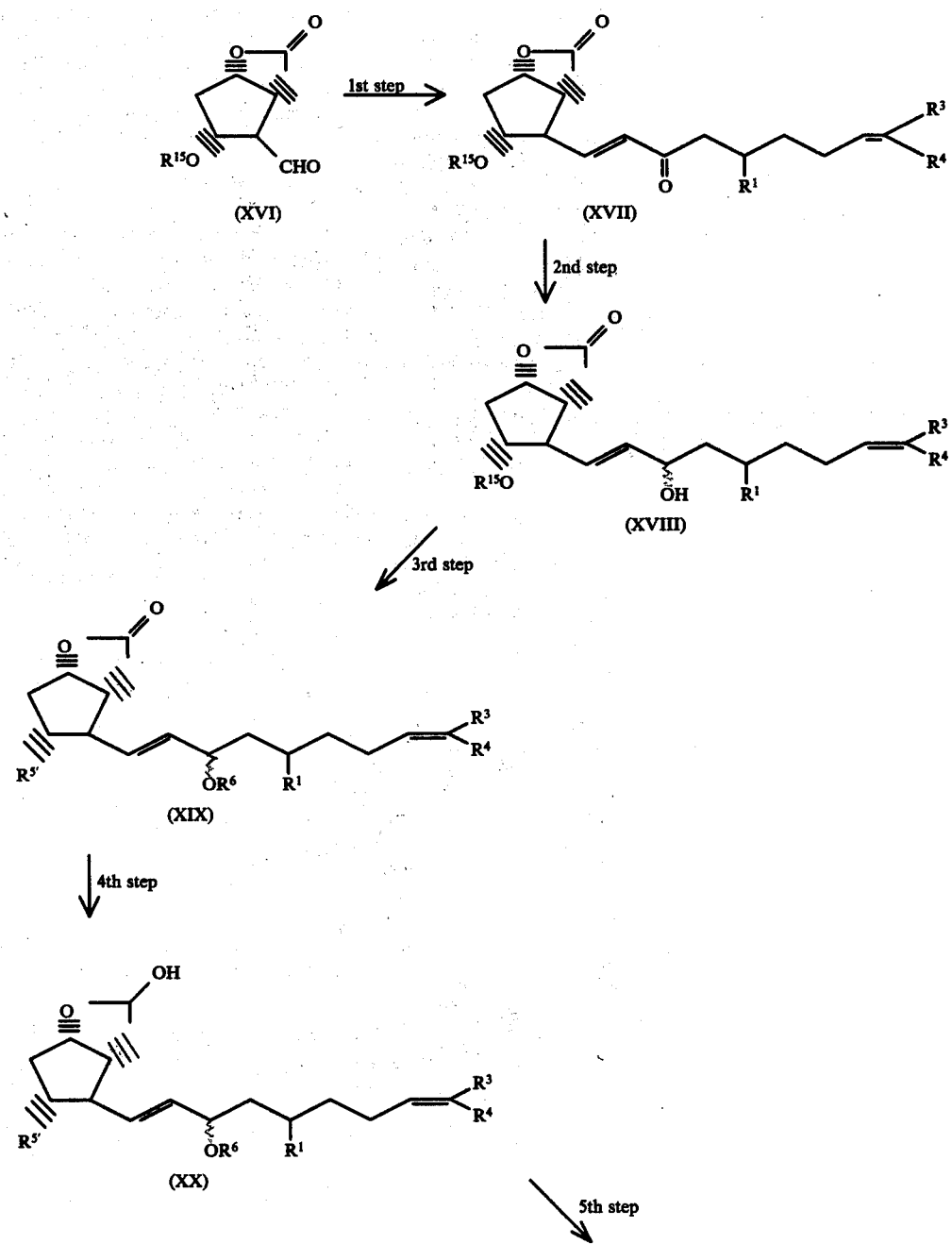

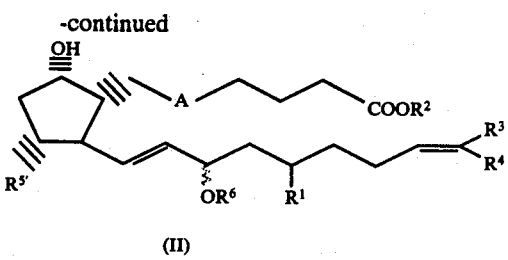

(II)

In the above formulae, A, $R^1$, $R^2$, $R^3$, $R^4$, $R^5$ and $R^6$ have the same meanings as defined hereinbefore. $R^{15}$ represents a protective group for the hydroxyl group, and there is no specific limitation on the protective group, so far as it shall not affect other moieties of the compound while the reaction for replacement of said protective group with a hydrogen atom shall be later on performed. Such a protective group is the same as the protective group hereinbefore stated for $R^6$.

Each of the steps will be explained by referring as the starting compound to the known compound of the general formula (XVI) which is described in J. Am. Chem. Soc., 91, 5675 (1969), below.

The first step is directed to the preparation of a compound having the aforementioned general formula (XVII), and can be performed by reacting a compound of the aforementioned general formula (XVI) with a Wittig reagent of the aforementioned general formula (XV). The present reaction conditions are the same as those in the seventh step for the preparation of a compound of the aforementioned general formula (XII).

The second step is directed to the preparation of a compound having the aforementioned general formula (XVIII), and can be performed by reducing a compound of the aforementioned general formula (XVII). The present reaction conditions are the same as those in the eighth step for the preparation of a compound of the aforementioned general formula (XIII).

The third step is directed to the preparation of a compound having the aforementioned general formula (XIX), and can be performed by changing $R^{15}$ of the protective group for the hydroxyl group of a compound of the aforementioned general formula (XVIII) and protecting the hydroxyl group of the resulting compound. The present reaction conditions are the same as those in the ninth step for the preparation of a compound of the aforementioned general formula (XIV).

The fourth step is directed to the preparation of a compound having the aforementioned general formula (XX), and can be performed by reducing a compound of the aforementioned general formula (XIX).

The fifth step is directed to the preparation of a compound having the aforementioned general formula (II), and can be performed by reacting a compound of the aforementioned general formula (XX) with a Wittig reagent of the general formula $$(R^{16})_3P^+ - CH^- - (CH_2)_3 - COOM_2 \qquad (XXI)$$

in which $R^{16}$ represents a hydrocarbon group such as an aryl group, e.g., phenyl, and an alkyl group e.g., n-butyl, and $M_2$ represents an alkali metal such as sodium and potassium, converting the resulting compound into a free acid by treatment with an acid in accordance with the conventional procedure, and, if necessary, esterifying the carboxyl group of the resulting free acid.

The reaction for esterifying the carboxyl group of the resulting free acid, which is performed if necessary, is carried out by bringing the free acid into contact with an esterifying agent. The present reaction conditions are the same as those in the tenth step for the preparation of a compound of the aforementioned general formula (II).

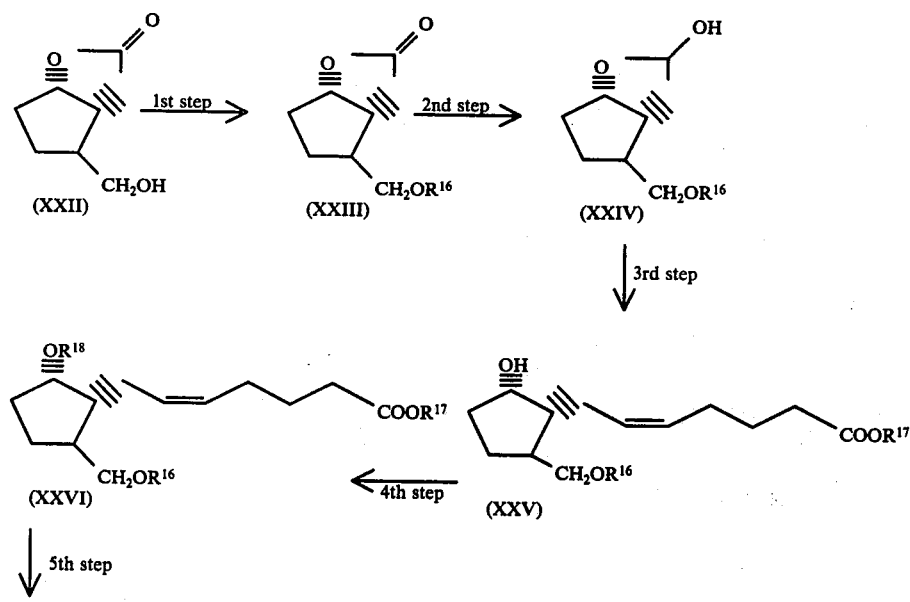

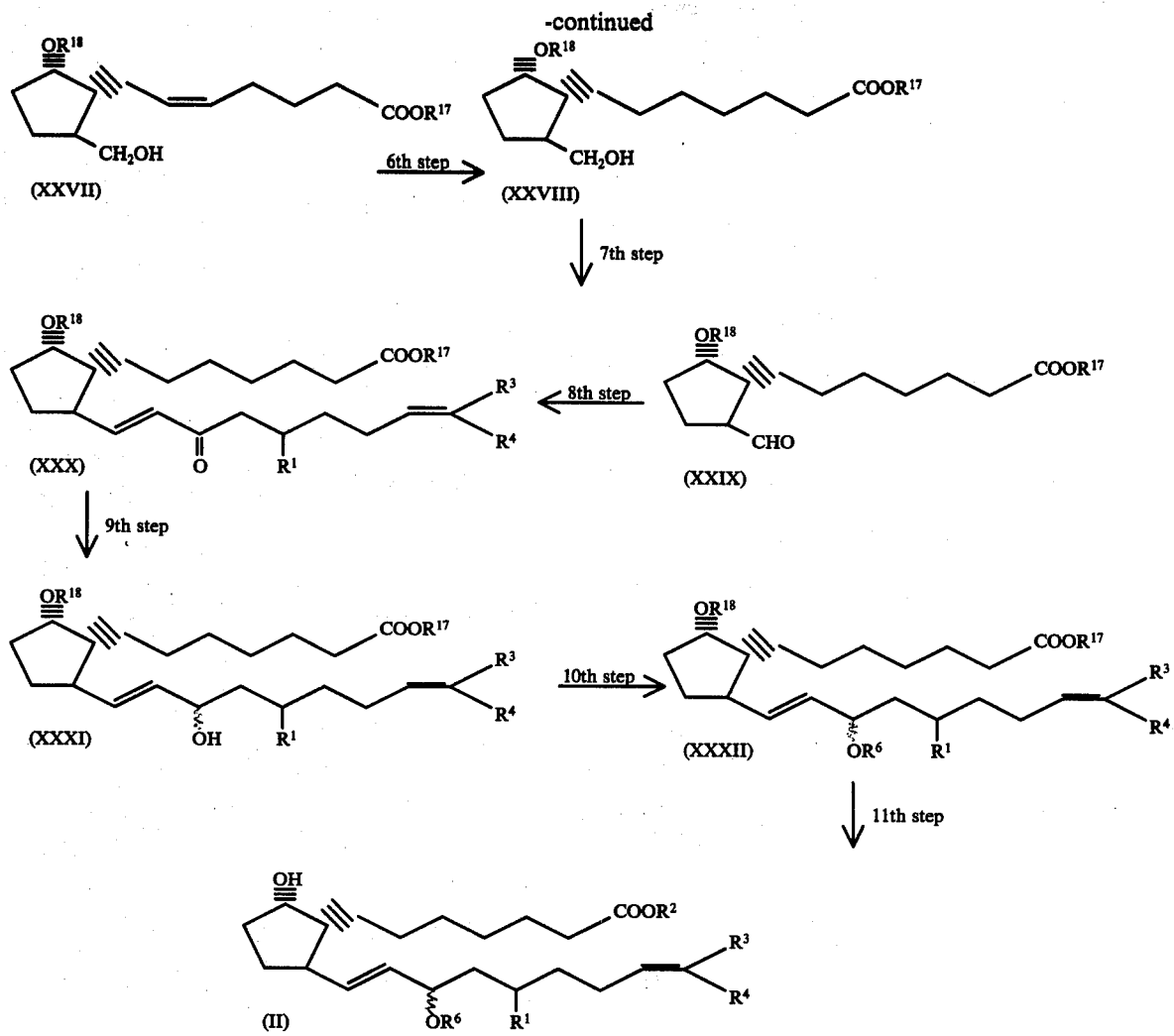

In the above formulae, $R^1$, $R^2$, $R^3$, $R^4$ and $R^6$ have the same meanings as defined hereinbefore. $R^6$ of the protective group for the hydroxyl group shall, however, remain unremoved while $R^{18}$ of the protective group for another hydroxyl group is removed. Each of $R^{16}$ and $R^{18}$ represents a protective group for each of the hydroxyl groups. There is no specific limitation on the protective group for the hydroxyl group so far as it does not affect other moieties while said protective group shall be later on replaced with a hydrogen atom. Such a protective group may be exemplified by the protective groups as hereinbefore stated for $R^6$. The protective group $R^{18}$ may preferably be an acyl group such as acetyl, n-propionyl, isopropionyl, n-butyryl, isobutyryl, benzoyl, 4-nitrobenzoyl, 2-chlorobenzoyl, 2,4-dichlorobenzoyl and phenylacetyl. $R^{17}$ represents a protective group for the carboxyl group. There is no specific limitation on the protective group for the carboxyl group so far as it does not affect other moieties while said protective group shall be later on replaced with a hydrogen atom. Such a protective group may be exemplified by a hydrocarbon group, for instance, methyl, ethyl, n-propyl, isopropyl, n-butyl, isobutyl, phenyl and benzyl, a halogenated alkyl group, for instance, 2,2,2-trichloroethyl, and a heterocyclic group, for instance, 2-tetrahydropyranyl, 2-tetrahydrothioyranyl, 2-tetrahydrofuranyl and 4-methoxytetrahydropyran-4-yl. However, the abovementioned protective groups are not limitative.

Each of the steps will be explained below, by referring as the starting compound to the known compound of the general formula (XXII) stated in Tetrahedron Letters, 1972, 115.

The first step is directed to the preparation of a compound having the formula (XXIII), and involves the reaction for obtaining a compound of the aforementioned general formula (XXII) in which the hydroxyl group is protected.

The second step is directed to the preparation of a compound having the aforementioned general formula (XXIV), and can be performed by reducing a compound having the aforementioned general formula (XXIII). The present reaction is carried out in the presence of a reducing agent. The reducing agent employed may preferably be a metal hydride, for instance, diisobutylaluminum hydride, sodium boron hydride, potassium boron hydride, lithium boron hydride, lithium tri-tert-butoxyaluminum hydride and lithium trimethoxyaluminum hydride.

The third step is directed to the preparation of a compound having the aforementioned general formula (XXV), and can be performed by reacting a compound of the aforementioned general formula (XXIV) with a Wittig reagent of the general formula $$(R^{19})_3 P^+ - CH^- - (CH_2)_3 - COOM_3 \quad (XXXIII)$$

in which R[19] represents a hydrocarbon group such as an aryl group, e.g., phenyl, and an alkyl group, e.g., n-butyl, and M₃ represents an alkali metal such as sodium and potassium, converting the resulting compound into a free acid by treatment with an acid in accordance with the conventional procedure, and protecting the carboxyl group of the resulting free acid.

The reaction for protecting the carboxyl group is carried out in the presence or absence of a solvent by bringing the compound into contact with a compound capable of forming a protective group for a carboxyl group.

The fourth step is directed to the preparation of a compound having the aforementioned general formula (XXVI), and can be performed by protecting the hydroxyl group of a compound of the aforementioned general formula (XXV).

The fifth step is directed to the preparation of a compound having the aforementioned general formula (XXVII), and can be performed by removing the protective group R[16] from the hydroxyl group of a compound of the aforementioned general formula (XXVI). The acid or base and the reaction condition adopted in the present reaction are the same as hereinbefore stated for the reaction for removal of the protective group from the hydroxyl group of a compound having the aforementioned general formula (III).

The sixth step is directed to the preparation of a compound having the aforementioned general formula (XXVIII), and can be performed by reducing a compound of the aforementioned general formula (XXVII). The present reaction is conducted using a reducing agent in the presence of a solvent. There is no specific limitation on the reducing agent employed, so far as it is included in the reducing agents which can convert the double bond into an ethylene group without reducing the carbonyl group. Preferably, a catalytic reduction using hydrogen is employed in the presence of a catalyst such as palladium-carbon and platinum oxide.

The seventh step is directed to the preparation of a compound having the aforementioned general formula (XXIX), and can be performed by oxidizing a compound of the aforementioned general formula (XXVIII). The present reaction is carried out in the presence of an oxidizing agent. The oxidizing agent and the reaction condition employed in the present reaction are the same as hereinbefore stated for the reaction for oxidizing a compound of the aforementioned general formula (II) into a compound of the aforementioned general formula (III).

The eighth step is directed to the preparation of a compound having the aforementioned general formula (XXX), and can be performed by reacting a compound of the aforementioned general formula (XXIX) with a Wittig reagent of the general formula

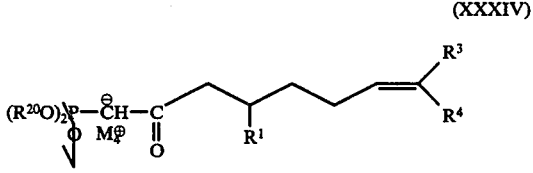

(XXXIV)

in which R¹, R³ and R⁴ have the same meanings as defined hereinbefore, R²⁰ represents an alkyl group, e.g., methyl, or an aryl group, e.g., phenyl, and M₄⁺ represents as metal ion, e.g., ions of sodium, potassium and lithium.

The ninth step is directed to the preparation of a compound having the aforementioned general formula (XXXI), and can be performed by reducing a compound of the aforementioned general formula (XXX). The reaction is carried out using a reducing agent in the presence or absence of a solvent. There is no specific limitation on the reducing agent employed, so far as it is included in the reducing agents which can convert the carbonyl group into an hydroxyl group without reducing the double bond. Such reducing agents may preferably be metal hydrides such as sodium boron hydride, potassium boron hydride, lithium boron hydride, zinc boron hydride, lithium tri-tert-butoxyaluminum hydride, lithium trimethoxyaluminum hydride, sodium cyanoboron hydride and lithium 9b-boraperhydrophenalene hydride.

The tenth step is directed to the preparation of a compound having the aforementioned general formula (XXXII), and can be performed by protecting the hydroxyl group of a compound of the aforementioned general formula (XXXI). There is no specific limitation on the protective group for the hydroxyl group so far as it shall not be simultaneously removed when R[18] of the protective group for another hydroxyl group shall be later on removed. The compound capable of forming the protective group and the reaction conditions are the same as hereinbefore stated in the first step.

The eleventh step is directed to the preparation of a compound having the aforementioned general formula (II), and can be performed by removing the protective groups R[18] and R[17] from the hydroxyl and carboxyl groups of a compound of the aforementioned general formula (XXXII) and then, if necessary, esterifying the carboxyl group of the resulting compound. In a certain case, the reaction for removal of the protective group R[17] from the carboxyl group may not be required, after the reaction for removal of the protective group R[18] from the hydroxyl group. That is because, in some case, the protective group R[17] may simultaneously be removed from the carboxyl group while the reaction for removal of the protective group R[18] from the hydroxyl group is conducted.

The reaction for removing the protective group R[18] from the hydroxyl group may easily be performed by bringing the compound into contact with either an acid or a base.

The reaction for removal of the protective group R[17] from the carboxyl group varies dependent upon the kind of the protective group.

The reaction for esterifying the carboxyl group, which is conducted, if necessary, is performed by bringing the compound into contact with an esterifying agent in the presence or absence of a solvent.

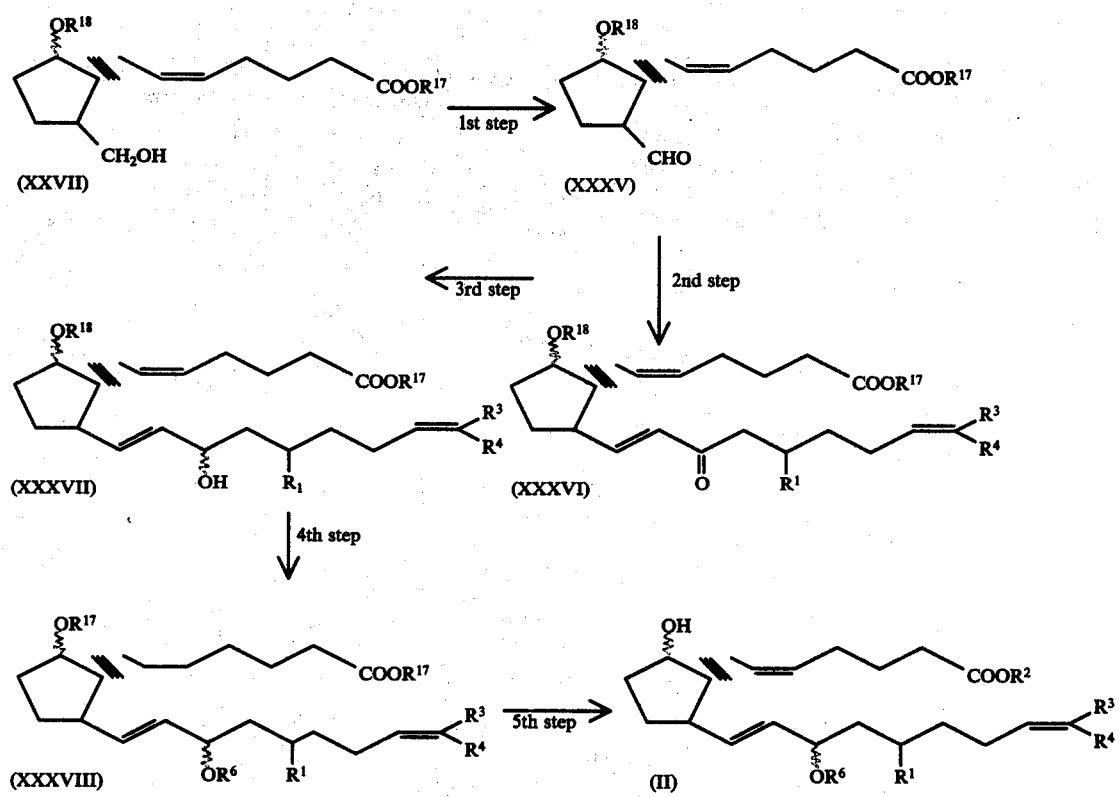

In the above formulae, $R^1$, $R^2$, $R^3$, $R^4$, $R^6$, $R^{17}$ and $R^{18}$ have the same meanings as defined hereinbefore.

Each of the steps will be explained below, by referring as the starting compound to a compound of the aforementioned general formula (XXVII) prepared in the aforementioned fifth step.

The first step is directed to the preparation of a compound having the aforementioned general formula (XXXV), and can be performed by oxidizing a compound of the aforementioned general formula (XXVII). The present reaction conditions are the same as those in the seventh step for the preparation of a compound having the aforementioned general formula (XXIX).

The second step is directed to the preparation of a compound having the aforementioned general formula (XXXVI), and can be performed by reacting a compound of the aforementioned general formula (XXXV) with a Wittig reagent of the aforementioned general formula (XXXIV). The present reaction conditions are the same as those in the eighth step for the preparation of a compound having the aforementioned general formula (XXX).

The third step is directed to the preparation of a compound having the aforementioned general formula (XXXVII), and can be performed by reducing a compound of the aforementioned general formula (XXXVI). The present reaction conditions are the same as those in the ninth step for the preparation of a compound having the aforementioned general formula (XXXI).

The fourth step is directed to the preparation of a compound having the aforementioned general formula (XXXVIII), and can be performed by protecting the hydroxyl group of a compound of the aforementioned general formula (XXXVII). The present reaction conditions are the same as those in the tenth step for the preparation of a compound of the aforementioned general formula (XXXII).

The fifth step is directed to the preparation of a compound having the aforementioned general formula (II), and can be performed by removing the protective group $R^{18}$ and $R^{17}$ from the hydroxyl and carboxyl groups of a compound of the aforementioned general formula (XXXVIII) and then, if necessary, esterifying the carboxyl group of the resulting compound. The present reaction conditions are the same as those in the eleventh step for the preparation of a compound having the aforementioned general formula (II).

In the above-explained steps, each of the desired compounds can be obtained by treating the reaction mixture in the usual manner, after completion of the reaction. The desired compounds thus obtained may be further purified by such conventional procedures as column chromatography and thin layer chromatography.

In addition, the desired compounds obtained above are in a mixture of the various geometrical isomers and/or optical isomers, and they may be isolated or resolved in an appropriate synthetic step.

The present invention will be further concretely illustrated by the following examples and referential examples.

EXAMPLE 1

9-Oxo-11α,15α-dihydroxy-17β-methyl-2-iso-propylideneprost13(trans)-enoic acid

1. In 20 ml of acetone was dissolved 766 mg of 9β-hydroxy-11α,15α-di(2-tetrahydropyranyloxy)-17β-methyl-20-isopropylideneprost-13(trans)-enoic acid. To this solution was added at $-11 \sim -13°$ C, 1 ml of Jones reagent (prepared by dissolving 26.72 g of chromic anhydride in 23 ml of sulfuric acid which was then mixed with a certain amount of water until the total amount reached 100 ml), and the resulting mixture was stirred for 20 minutes. After completion of the reaction, an excess of the reagent was decomposed by addition of isopropyl alcohol, and the solution was, after addition of water, extracted with ethyl acetate. The extract was washed with water and dried over anhydrous sodium sulfate. The solvent was then evaporated from the extract under reduced pressure to leave 652 mg of 9-oxo-11α,15α-di(2-tetrahydropyranyloxy)-17β-methyl-20-isopropylideneprost-13-(trans)-enoic acid as an oil.

IR spectrum (liquid film) $\nu_{max}$ cm$^{-1}$: 1745, 1712.

NMR spectrum (CCl$_4$) δ ppm: 0.90 (3H, doublet, J=6 Hz), 5.0 (1H, triplet, J=6 Hz), 5.55 (2H, multiplet).

2. In a mixture of acetic acid, water and tetrahydrofuran (15 ml, 15 ml and 5 ml, respectively) was dissolved 652 mg of 9-oxo-11α,15α-di(2-tetrahydropyranyloxy)-17β-methyl-20-isopropylideneprost-13(trans)-enoic acid, and the resulting solution was stirred at 35° C for 4.5 hours. After completion of the reaction, the reaction mixture was, after addition of water, extracted with ethyl acetate. The extract was washed with water and dried over anhydrous sodium sulfate. The solvent was evaporated from the extract to leave 640 mg of the residue. The residue was then purified on a column of silica gel to give 210 mg of 9-oxo-11α,15α- dihydroxy-17β-methyl-20-isopropylideneprost-13(trans)-enoic acid as an oil.

IR spectrum (liquid film) $\nu_{max}$ cm$^{-1}$: 3380, 1735, 1710.

NMR spectrum (CDCl$_3$) δ ppm: 0.90 (3H, doublet, J=6 Hz), 1.58 (3H, singlet), 1.62 (3H, singlet), 4.10 (2H, multiplet), 5.57 (2H, multiplet)

3. Potassium salt

In 10 ml of 30% aqueous alcohol was dissolved 408 mg of the above obtained carboxylic acid. To this solution was added 100 mg of potassium hydrogen carbonate in 10 ml of 30% aqueous methanol, and the resulting mixture was then stirred at room temperature for one hour. After completion of the reaction, the solvent was evaporated at a low temperature to leave 507 mg of potassium 9-oxo-11α,15α-dihydroxy-17β-methyl-20-isopropylideneprost-13(trans)-enoate as an oil.

IR spectrum (liquid film) $\nu_{max}$ cm$^{-1}$: 1595

EXAMPLE 2

9-Oxo-11α,15β-dihydroxy-17β-methyl-20-isopropylideneprost-13(trans)-enoic acid 1. 764 mg of 9β-hydroxy-11α,15β-di(2-tetrahydropyranyloxy)-17β-methyl-20-isopropylideneprost-13(trans)-enoic acid was reacted and treated in the same manner as in Example 1 - (1) to give 750 mg of 9-oxo-11α,15β-di(2-tetrahydropyranyloxy)-17β-methyl-20-isopropylideneprost-13(trans)-enoic acid as an oil.

IR spectrum (liquid film $\nu_{max}$ cm$^{-1}$: 1739, 1708.

NMR spectrum (CCl$_4$) δ ppm: 0.90 (3H, doublet, J=6 Hz), 5.03 (1H, triplet, J=6 Hz), 5.50 (2H, multiplet)

2. 750 mg of 9-oxo-11α,15β-di(2-tetrahydropyranyloxy)-17β-methyl-20-isopropylideneprost-13(trans)-enoic acid was reacted and treated in the same manner as in Example 1 - (2) to give 163 mg of 9-oxo-11α,15β-dihydroxy-17β-methyl-20-isopropylideneprost-13(trans)-enoic acid as an oil.

IR spectrum (liquid film) $\nu_{max}$ cm$^{-1}$: 3400, 1730, 968.

NMR spectrum (CDCl$_3$) δ ppm: 0.91 (3H, doublet, J=6 Hz), 1.58 (3H, singlet), 1.64 (3H, singlet), 4.10 (2H, multiplet), 5.66 (2H, multiplet).

EXAMPLE 3

Methyl 9-oxo-11α,15α-dihydroxy-17β-methyl-20-isopropylideneprost-13(trans)-enoate 1. 351 mg of methyl 9β-hydroxy-11α,15α-di(2-tetrahydropyranyloxy)-17β-methyl-20-isopropylideneprost-13(trans)-enoate was reacted and treated in the same manner as in Example 1 - (1) to give 298 mg of methyl 9-oxo-11α,15α-di(2-tetrahydropyranyloxy)17β-methyl-20-isopropylideneprost-13(trans)-enoate as an oil.

IR spectrum (liquid film) $\nu_{max}$ cm$^{-1}$: 1746.

NMR spectrum (CCl$_4$) δ ppm 0.91 (3H, doublet, J=6 Hz), 3.68 (3H, singlet), 5.01 (1H, triplet, J=6 Hz), 5.55 (2H, multiplet)

2. 280 mg of methyl 9-oxo-11α,15α-di(2-tetrahydropyranyloxy)-17β-methyl-20-isopropylideneprost-13(trans)-enoate was reacted and treated in the same manner as in Example 1 —(2) to give 71 mg of methyl 9-oxo-11α,15α-dihydroxy-17β-methyl-20-isopropylideneprost-13(trans)-enoate as an oil.

IR spectrum (liquid film) $\nu_{max}$ cm$^{-1}$: 3380, 1735.

NMR spectrum (CD$_3$COCD$_3$) δ ppm: 0.90 (3H, doublet, J=6 Hz), 3.67 (3H, singlet), 5.57 (2H, multiplet).

EXAMPLE 4

9-Oxo-11α,15α-dihydroxy-17β-methyl-20-isopropylidene-prost-5(cis), 13(trans)-dienoic acid 1. In 20 ml of acetone was dissolved 750 mg of 9α-hydroxy-11α, 15α-di(2-tetrahydropyranyloxy)-17β-methyl-20-isopropylideneprost-5(cis), 13(trans)-dienoic acid, and the resulting solution was, after addition of 1 ml of Jones reagent at about −13° C, stirred for 20 minutes. After completion of the reaction, an excess of the reagent was decomposed by addition of isopropyl alcohol. The solution was, after addition of water, extracted with ethyl acetate. The extract was washed with water and dried over anhydrous sodium sulfate. The solvent was then evaporated from the extract to leave 631 mg of 9-oxo-11α, 15α-di(2-tetrahydropyranyloxy)-17β-methyl-20-isopropylideneprost-5(cis), 13(trans)-dienoic acid as an oil.

IR spectrum (liquid film) $\nu_{max}$ cm$^{-1}$: 1745, 1710.

NMR spectrum (CCl$_4$) δ ppm: 0.91 (3H, doublet, J=6 Hz).

2. In a mixture of acetic acid, water and tetrahydrofuran (15 ml, 15 ml, 5 ml, respectively) was dissolved 625 mg of 9-oxo-11α, 15α-di(2-tetrahydropyranyloxy)-17β-methyl-20-isopropylideneprost-5(cis), 13(trans)-dienoic acid, and the solution was stirred at 35° C for 4 hours. After completion of the reaction, the reaction mixture was washed with water and dried over anhydrous sodium sulfate. The solvent was evaporated from the extract to leave 610 mg of the residue. The residue was then purified on a column of silica gel to give 203 mg of 9-oxo-11α, 15α-dihydroxy-17β-methyl-20-isopropylideneprost-5-(cis), 13(trans)-dienoic acid as an oil.

IR spectrum (liquid film) $\nu_{max}$ cm$^{-1}$: 3380, 1740, 1710.

NMR spectrum (CD$_3$COCD$_3$) δ ppm: 0.91 (3H, doublet, J=6 Hz), 1.59 (3H), 1.65 (3H), 4.11 (2H, multiplet), 5.38 (2H, multiplet), 5.65 (2H, multiplet).

EXAMPLE 5

9-Oxo-11α,15αβ-dihydroxy-17β-methyl-20-isopropylideneprost-5(cis),13(trans)-dienoic acid 1. 9α-Hydroxy-11α,15β-di(2-tetrahydropyranyloxy)17β-methyl-20-isopropylideneprost-5(cis),13(trans)-dienoic acid was reacted and treated in the same manner as in Example 4 - (1) to give 9-oxo-11α,15β-di(2-tetrahydropyranyloxy)-17β-methyl-20-isopropylideneprost5(cis),13(trans)-dienoic acid as an oil.

IR spectrum (liquid film) $\nu_{max}$ cm$^{-1}$: 1745, 1710.

NMR spectrum (CCl$_4$) δ ppm: 0.91 (3H, doublet, J=6 Hz). 2. 9-Oxo-11α, 15β-di(2-tetrahydropyranyloxy)-17β-methyl-20-isopropylidenesprost-5(cis), 13(trans)-dienoic acid was reacted and treated in the same manner as in Example 4 - (2) to give 9-oxo-11α, 15β-dihydroxy-17β-methyl-20-isopropylideneprost-5(cis), 13(trans)-dienoic acid as an oil.

IR spectrum (liquid film) $\nu_{max}$ cm$^{-1}$: 3380, 1730, 1710.

NMR spectrum (CD$_3$COCD$_3$) δ ppm: 0.91 (3H, doublet, J=6 Hz), 1.59 (3H, singlet), 1.63 (3H, singlet), 4.15 (2H, multiplet), 5.43 (2H, multiplet), 5.69 (2H, multiplet)

EXAMPLE 6

Methyl 9-oxo-11α, 15α-dihydroxy-17β-methyl-20-isopropylideneprost-5(cis), 13(trans)-dienoate 1. 751 mg of methyl 9α-hydroxy-11α, 15α-di(2-tetrahydropyranyloxy)-17β-methyl-20-isopropylideneprost-5(cis), 13(trans)-dienoate was reacted and treated in the same manner as in Example 4 - (1) to give 630 mg of methyl 9-oxo-11α, 15α-di(2-tetrahydropyranyloxy)-17β-methyl-20-isopropylideneprost-5(cis), 13(trans)-dienoate as an oil.

IR spectrum (liquid film) $\nu_{max}$ cm$^{-1}$: 1745.

NMR spectrum (CCl$_4$) δ ppm: 0.90 (3H, doublet, J=6 Hz), 3.67 (3H, singlet).

2. 610 mg of methyl 9-oxo-11α, 15α-di(2-tetrahydropyranyloxy)-17β-methyl-20-isopropylideneprost-5(cis), 13(trans)-dienoate was reacted and treated in the same manner as in Example 4 - (2) to give 190 mg of methyl 9-oxo-11α, 15α-dihydroxy-17β-methyl-20-isopropylideneprost-5(cis), 13(trans)-dienoate as an oil.

IR spectrum (liquid film) $\nu_{max}$ cm$^{-1}$: 3400, 1736.

NMR spectrum (CD$_3$COCD$_3$) δ ppm: 0.90 (3H, doublet, 6 Hz), 1.58 (3H, singlet), 1.60 (3H, singlet), 3.67 (3H, singlet), 5.38 (2H, multiplet), 5.65 (2H, multiplet).

EXAMPLE 7

9-Oxo-11α, 15α-dihydroxy-20-isopropylideneprost-13(trans)-enoic acid and 9-oxo-11α, 15β-dihydroxy-20-isopropylideneprost-13(trans)-enoic acid 1. 1.01 g of 9β-hydroxy-11α, 15-di(2-tetrahydropyranyloxy)-20-isopropylideneprost-13(trans)-enoic acid was reacted and treated in the same manner as in Example 1 - (1) to give 910 mg of 9-oxo-11α, 15-di(2-tetrahydropyranyloxy)-20-isopropylideneprost-13(trans)-enoic acid as an oil.

IR spectrum (liquid film) $\nu_{max}$ cm$^{-1}$: 1710, 1040, 1020.

NMR spectrum (CCl$_4$) δ ppm: 5.54 (2H, multiplet).

2. 910 mg of 9-oxo-11α, 15-di(2-tetrahydropyranyloxy)-20-isopropylideneprost-13(trans)-enoic acid was reacted and treated in the same manner as in Example 1 - (2) to give a crude product. The obtained crude product was purified by means of preparative thin layer chromatography and by using a mixture of benzene, dioxane and acetic acid (18 : 12 : 1) as a developing solvent. There were obtained 9-oxo-11α, 15α-dihydroxy-20-isopropylideneprost-13(trans)-enoic acid as an oil from the more polar portion and 9-oxo-11α, 15β-dihydroxy-20-isopropylideneprost-13(trans)-enoic acid from the less polar eluates.

15α-Isomer

IR spectrum (liquid film) $\nu_{max}$ cm$^{-1}$: 3360, 1735, 1710, 970.

NMR spectrum (CD$_3$COCD$_3$) δ ppm: 1.58 (3H, singlet), 1.66 (3H, singlet), 5.58 (2H, multiplet).

15β-Isomer

IR spectrum (liquid film) $\nu_{max}$ cm$^{-1}$: 3370, 1735, 1710, 980

NMR spectrum (CD$_3$COCD$_3$) δ ppm: 1.59 (3H, singlet), 1.66 (3H, singlet), 5.64 (2H, multiplet)

EXAMPLE 8

9-Oxo-11α, 15α-dihydroxy-20-isopropylideneprost-5(cis), 13(trans)-dienoic acid 1. In 300 ml of acetone was dissolved 12.9 g of 9α-hydroxy-11α, 15α-di(2-tetrahydropyranyloxy)-20-isopropylideneprost-5(cis), 13(trans)-dienoic acid. To the solution was added at −20° C., 25 ml of Jones reagent. The mixture was stirred for one hour at −20° C. After completion of the reaction, the mixture was poured into 2 l of ice water. The mixture was extracted with ether and the extract was dried over anhydrous sodium sulfate. The solvent was distilled off to give 10.3 g of oil. The oil was purified by column chromatography using 100 g of silica gel to give 8.41 g of 9-oxo-11α, 15α-di(2-tetrahydropyranyloxy)-20-isopropylideneprost-5(cis), 13(trans)-dienoic acid as an oil.

IR spectrum (liquid film) $\nu_{max}$ cm$^-$: 1745, 1710, 1135, 1020, 970.

NMR spectrum (CDCl$_3$) δ ppm: 4.7 (2H, multiplet) 5.0 – 5.8 (5H, multiplet).

2. In a mixture of 100 ml of acetic acid, 100 ml of water and 30 ml of tetrahydrofuran was dissolved 8.41 g of 9-oxo-11α, 15α-di(2-tetrahydropyranyloxy)-20-isopropylideneprost-5(cis), 13(trans)-dienoic acid. The solution was stirred at 40° C. for 1.5 hours. After addition of 100 ml of water, the solution was heated at 40° C. for 1.5 hours. The solution was diluted with 500 ml of aqueous saturated sodium chloride and extracted with a mixture of ethyl acetate and benzene (1 : 1). The extract was washed with aqueous saturated sodium chloride and the solvent was distilled off to give 6.9 g of oil. The oil was purified by column chromatography using 100 g of silica gel to afford 2.8 g of crystals. The crystals were recrystallized from a mixture of ethyl acetate and hexane to give 2.1 g of 9-oxo-11α, 15α-dihydroxy-20-isopropylideneprost-5(cis), 13(trans)-dienoic acid as crystals melting at 64°– 66° C.

IR spectrum (liquid paraffin) $\nu$ max cm$^{-1}$: 3380, 1730, 1705, 1160, 970

NMR spectrum (CD$_3$COCD$_3$) δ ppm: 4.08 (2H, multiplet), 5.17 (1H, triplet), 5.42 (2H, multiplet), 5.68 (2H, multiplet).

Mass spectrum m/e : 392.

EXAMPLE 9

9-Oxo-11α, 15β-dihydroxy-20-isopropylideneprost-5(cis), 13(trans)-dienoic acid

1. Following the same procedure as in Example 8 - (1), but replacing 9α-hydroxy-11α, 15α-di(2-tetrahydropyranyloxy)-20-isopropylideneprost-5(cis), 13(trans)-dienoic acid with 6.5 g of 9α-hydroxy-11α, 15β-di(2-tetrahydropyranyloxy)-20-isopropylideneprost-5(cis), 13(trans)-dienoic acid, there was obtained 4.1 g of 9-oxo-11α, 15β-di(2-tetrahydropyranyloxy)-20-isopropylideneprost-5(cis), 13(trans)-dienoic acid as an oil.

IR spectrum (liquid film) $\nu_{max}$ cm$^-$ : 1745, 1710, 1135, 1020, 970

NMR spectrum (CDCl$_3$) δ ppm: 4.7 (2H, multiplet) 5.0 – 5.8 (5H, multiplet)

2. Following the same procedure as in Example 8 - (2), but replacing 9-oxo-11α, 15α-di(2-tetrahydropyranyloxy)-20-isopropylideneprost-5(cis), 13(trans)-dienoic acid with 4.2 g. of 9-oxo-11α, 15β-di(2-tetrahydropyranyloxy)-20-isopropylideneprost-5(cis), 13(trans)-dienoic acid, there was obtained 1.2 g of 9-oxo-11α, 15β-dihydroxy-20-isopropylideneprost-5(cis), 13(trans)-dienoic acid as an oil.

IR spectrum (liquid film) $\nu_{max}$ cm$^{-1}$: 3380, 1730, 1160, 970.

NMR spectrum (CD$_3$COCD$_3$) δ ppm: 4.07 (2H, multiplet), 5.15 (1H, triplet) 5.4 (2H, multiplet), 5.68 (2H, multiplet).

Mass spectrum m/e : 392.

EXAMPLE 10

Methyl 9-oxo-15α(or β)-hydroxy-20-isopropylideneprost-13(trans)-enoate 1. 9-Oxo-15-(2-tetrahydropyranyloxy)-20-isopropylideneprost-13(trans)-enoic acid In 80 ml of acetone was dissolved 2.6 g of 9α-hydroxy-15-(2-tetrahydropyranyloxy)-20-isopropylideneprost-13(trans)-enoic acid, and 5 ml of Jones oxidizing reagent was added thereto with stirring at −20° ∼ −10° C. The stirring was then continued at −20° ∼ 10° C for 30 minutes until the reaction terminated. The reaction mixture was diluted with 200 ml of ice-water and extracted with ether. The extract was washed with water and dried over anhydrous sodium sulfate. Upon evaporation of the solvent under reduced pressure, there was obtained 2.6 g of the desired compound as an oil.

IR spectrum (liquid film) $\nu_{max}$ cm$^{-1}$: 3200, 2750, 1740, 1710, 1200, 1130, 1110, 1020, 970.

NMR spectrum (CDCl$_3$) δ ppm: 5.55 (2H, multiplet), 5.10 (1H, multiplet), 4.70 (1H, multiplet).

2. Methyl 9-oxo-15α(or β)-hydroxy-20-isopropylideneprost-13(trans)-enoate

In 50% aqueous acetic was dissolved 2.6 g of 9-oxo-15-(2-tetrahydropyranyloxy)-20-isopropylidene-prost-13(trans)-enoic acid, and the solution was stirred at 50° C for 1.5 hours until the reaction terminated. The reaction mixture was then diluted with 200 ml of ice-water and extracted with ethyl acetate. The extract was washed with water and dried over anhydrous sodium sulfate. Upon evaporation of the solvent under reduced pressure, 2.2 g of an oily residue was obtained. To the residue was added an ethereal solution of diazomethane until the yellow color of the added diazomethane remained in the residue. The ether was evaporated to leave 2.23 g of an oily residue. The obtained residue was separated and purified by means of column chromatography and thin layer chromatography to give the desired 15α-hydroxy (730 mg) and 15β-hydroxy (680 mg) derivatives, each as an oil.

15α-Hydroxy derivative

IR spectrum (liquid film) $\nu_{max}$ cm$^{-1}$: 3480, 1740, 1200, 1170, 970.

NMR spectrum (CDCl$_3$) δ ppm: 3.65 (3H, singlet), 4.10 (1H, multiplet), 5.10 (1H, multiplet), 5.60 (2H, multiplet).

Mass spectrum m/e : 392.

15β-Hydroxy derivative

IR spectrum (liquid film) $\nu_{max}$ cm$^{-1}$: 3480, 1740, 1200, 1170, 970.

NMR spectrum (CDCl$_3$) δ ppm: 3.65 (3H, singlet), 4.10 (1H, multiplet), 5.13 (1H, multiplet), 5.60 (2H, multiplet).

Mass spectrum m/e : 392.

EXAMPLE 11

9-Oxo-15α-hydroxy-20-isopropylideneprost-13-(trans)-enoic acid

In 15 ml of methanol was dissolved 730 mg of methyl 9-oxo-15α-hydroxy-20-isopropylideneprost-13(trans)-enoate, and, after addition of 10 ml of 5% aqueous sodium hydroxide solution, the resulting solution was stirred at room temperature for 2 hours. After completion of the reaction, the reaction solution was diluted with 150 ml of ice-water. The solution was then neutralized with 7% aqueous hydrochloric acid and extracted with ethyl acetate. The extract was washed with water and dried over anhydrous sodium sulfate. Upon evaporation of the solvent under reduced pressure, 730 mg of an oily residue was obtained. The obtained residue was crystallized from ether and n-hexane to give 524 mg of the desired compound as crystals, m.p. 40° − 45° C.

IR spectrum (liquid film) $\nu_{max}$ cm$^{-1}$: 3400, 2670, 1740, 1720, 1460, 1410, 1280, 1220, 1160, 970.

NMR spectrum (CD$_3$COCD$_3$) δ ppm: 4.08 (1H, multiplet), 5.16 (1H, triplet), 5.64 (2H, multiplet), 6.50 (2H, multiplet).

Mass spectrum m/e : 378.

EXAMPLE 12

Potassium 9-oxo-15α-hydroxy-20-isopropylideneprost-13(trans)-enoate

In a mixture of 8 ml of methanol and 2 ml of water was dissolved 150 mg of 9-oxo-15α-hydroxy-20-isopropylideneprost-13(trans)-enoic acid, and, after addition of 28 mg of potassium carbonate, the resulting solution was stirred at room temperature for one hour. After completion of the reaction, the solvent was evaporated from the reaction solution under reduced pressure to give 170 mg of the desired compound as a powder.

IR spectrum (fluid paraffin) $\nu_{max}$ cm$^{-1}$: 3400, 1735, 1580 – 1560

EXAMPLE 13

9-Oxo-15β-hydroxy-20-isopropylideneprost-13(trans)-enoic acid 680 mg of methyl 9-oxo-15β-hydroxy-20-isopropylideneprost-13(trans)-enoate was reacted and treated in the same manner as in Example 11 to give 650 mg of the desired compound as an oil.

IR spectrum (liquid film) $\nu_{max}$ cm$^{-1}$: 3400, 2680, 1740, 1720, 1270, 1160, 970.

NMR spectrum (CD$_3$COCD$_3$) δ ppm: 4.08 (1H, multiplet), 5.12 (1H, triplet), 5.60 (2H, multiplet)

Mass spectrum m/e : 378

EXAMPLE 14

Methyl 9-oxo-15α-(or β)-hydroxy-20-isopropylideneprost-5(cis),13(trans)-dienoate 1. 9-Oxo-15-(2-tetrahydropyranyloxy)-20-isopropylideneprost-5-(cis), 13(trans)-dienoic acid 2.5 g of 9α-hydroxy-15-(2-tetrahydropyranyloxy)-20-isopropylideneprost-5(cis), 13(trans)-dienoic acid was reacted and treated in the same manner as in Example 10 - (1) to give 2.35 g of the desired compound as an oil.

IR spectrum (liquid film) $\nu_{max}$ cm$^{-1}$: 3200, 2650, 1740, 1710, 1130, 1015 970.

2. Methyl 9-oxo-15α(or β)-hydroxy-20-isopropylideneprost-5(cis), 13(trans)-dienoate 2.34 g of 9-oxo-15-(2-tetrahydropyranyloxy)-20-isopropylideneprost-5(cis), 13(trans)-dienoic acid was reacted and treated in the same manner as in Example 10 - (2) to give the desired 15α-hydroxy (0.70 g) and 15β-hydroxy (0.77 g) derivatives, each as an oil.

15α-Hydroxy isomer

IR spectrum (liquid film) $\nu_{max}$ cm$^{-1}$: 3450, 1740, 1435, 1200, 1155, 1010, 970

NMR spectrum (CDCl$_3$) δ ppm: 3.65 (3H, singlet), 4.08 (1H, multiplet), 5.08 (1H, triplet), 5.33 (2H, multiplet), 5.56 (2H, multiplet).

15β-Hydroxy isomer

IR spectrum (liquid film) $\nu_{max}$ cm$^{-1}$: 3480, 1740, 1430, 1240, 1215, 1155, 970.

NMR spectrum (CDCl$_3$) δ ppm:
3.65 (3H, singlet), 4.08 (1H, multiplet), 5.10 (1H, multiplet), 5.35 (2H, multiplet), 5.56 (2H, multiplet).

EXAMPLE 15

9-Oxo-15α-hydroxy-20-isopropylideneprost-5(cis), 13(trans)-dienoic acid

In 15 ml methanol was dissolved 690 mg of methyl 9-oxo-15α-hydroxy-20-isopropylideneprost-5(cis), 13-(trans)-dienoate, and, after addition of 15 ml of 5% aqueous sodium hydroxide solution, the resulting solution was stirred at room temperature for one hour. After completion of the reaction, the reaction solution was diluted with 100 ml of ice-water. The solution was then neutralized with 7% aqueous hydrochloric acid and extracted with ethyl acetate. The extract was washed with water and dried over anhydrous sodium sulfate. After evaporation of the solvent under reduced pressure, the oily residue was purified on column to give 511 mg of the desired compound as an oil.

IR spectrum (liquid film) $\nu_{max}$ cm$^{-1}$: 3400, 2650, 1740, 1710, 1400, 1230, 1150, 1060, 960

NMR spectrum (CD$_3$COCD$_3$) δ ppm: 4.04 (1H, multiplet), 5.12 (1H, multiplet) 5.32 (2H, multiplet), 5.57 (2H, multiplet)

Mass spectrum m/e : 376

EXAMPLE 16

9-Oxo-15β-hydroxy-20-isopropylideneprost-5(cis), 13(trans)-dienoic acid 765 mg of methyl-9-oxo-15β-hydroxy-20-isopropylideneprost-5(cis), 13(trans)-dienoate was reacted and treated in the same manner as in Example 15 to give 667 mg of the desired compound as an oil.

IR spectrum (liquid film) $\nu_{max}$ cm$^{-1}$: 3400, 2650, 1740, 1710, 1400, 1230, 1150, 1000, 960.

NMR spectrum (CD$_3$COCD$_3$) δ ppm: 4.03 (1H, multiplet), 5.10 (1H, multiplet), 5.36 (2H, multiplet), 5.60 (2H, multiplet).

Mass spectrum m/e : 3.76.

Referential example 1

9β-Hydroxy-11α,15α(or β)-di(2-tetrahydropyranyloxy)-17β-methyl-20-isopropylideneprost-13(trans)-enoic acid (II)

1. 1α-Acetoxy-2β-methoxycarbonyl-3α-(6-ethoxycarbonylhexyl)-4α-(1,1'-ethylenedithioethyl)cyclopentane (VI)

In 50 ml of dichloromethane was dissolved 22.14 g of 1α-acetoxy-2β-methoxycarbonyl-3α-(6-ethoxycarbonylhexyl)-4α-acetylcyclopentane (V). To this solution were added under ice-cooling 80 ml of ethylene dithioglycol and 16 ml of a boron trifluoroideethyl ether complex, and the mixture was stirred for 1 hour. After completion of the reaction, ice-water was added to the reaction mixture, and the resulting mixture was extracted with ether. The extract was washed with water, an aqueous potassium hydrogen carbonate solution and water, successively, and dried over anhydrous sodium sulfate. After the drying, the solvent was evaporated to leave a gum. The obtained gum was then purified on a column of silica gel and by developing with benzene and a benzene solution containing 5% of ethyl acetate. The eluates were combined and evaporated to remove the solvent, leaving 23.0 g of the desired compound as an oil.

IR spectrum (liquid film) $\nu_{max}$ cm$^{-1}$: 1738.

NMR spectrum (CDCl$_3$) δ ppm: 1.23 (3H, triplet), 1.78 (3H, singlet), 2.02 (3H, singlet), 3.70 (3H, singlet).

2. 1α-Hydroxy-2β-methoxycarbonyl-3α-(6-methoxycarbonylhexyl)-4α-(1,1'-ethylenedithioethyl)cyclopentane (VI)

In 250 ml of methanol were dissolved 23.0 g. of 1α-acetoxy-2β-methoxycarbonyl-3α-(6-ethoxycarbonylhexyl)-4α-(1,1'-ethylenedithioethyl)cyclopentane and 10 g of potassium carbonate, and the solution was stirred at room temperature for 2.5 hours. After completion of the reaction, the reaction mixture was, after addition of aqueous acetic acid, extracted with ether. The extract was washed with water and dried over anhydrous sodium sulfate. After drying, the solvent was evaporated to leave a gum. The obtained gum was purified on a column of silica gel and by developing with benzene and a benzene solution containing 30% of ethyl acetate. The eluates were combined and evaporated to remove the solvent, leaving 20.4 g of the desired compound as an oil.

IR spectrum (liquid film) $\nu_{max}$ cm$^{-1}$: 1730, 3450.

NMR spectrum (CDCl$_3$) δ ppm: 3.66 (3H, singlet), 3.70 (3H, singlet).

1α-(2-Tetrahydropyranyloxy)-2β-methoxycarbonyl-3α-(6-methoxycarbonylhexyl)-4α-(1,1'-ethylenedithioethyl)cyclopentane (VI)

In 120 ml of benzene was dissolved 20.4 g of 1α-hydroxy-2β-methoxycarbonyl-3α-(6-methoxycarbonylhexyl)-4α-(1,1'-ethylenedithioethyl)cyclopentane. To this solution were added under ice-cooling 70 ml of dihydropyran and a catalytic amount of picric acid, and the resulting mixture was stirred for 15 hours. After completion of the reaction, the solvent was evaporated from the reaction mixture to leave a gum. The obtained gum was purified on a column of neutral alumina (Woelm Co. product Grade II 350 g) and by developing a hexane solution containing 10% of benzene and a benzene solution containing 5% of ethyl acetate. The eluates were combined and evaporated to remove the solvent, leaving 21.44 g of the desired compound as an oil.

IR spectrum (liquid film) $\nu_{max}$ cm$^{-1}$: 1030, 1730.

NMR spectrum (CCl$_4$) δ ppm: 3.60 (3H, singlet), 3.65 (3H, singlet).

4.

1α-(2-Tetrahydropyranyloxy)-2β-methoxycarbonyl-3α-(6-carboxyhexyl)-4α-(1,1'-ethylenedithioethyl)-cyclopentane (VII)

In 200 ml of 30% aqueous methanol containing 5% of potassium carbonate was dissolved 3.4 g of 1α-(2-tetrahydropyranyloxy)-2β-methoxycarbonyl-3α-(6-methoxycarbonylhexyl)-4α-(1,1'-ethylenedithioethyl)-cyclopentane, and the solution was stirred at room temperature for 4 hours and 40 minutes. After completion of the reaction, water was added to the reaction mixture and the resulting mixture was then extracted with hexane. Further, the aqueous portion was acidified with acetic acid and extracted with ether. The extract was washed with water and dried over anhydrous sodium sulfate. After drying the solvent was evaporated from the extract to leave 2.4 g of the desired compound as an oil.

IR spectrum (liquid film) $\nu_{max}$ cm$^{-1}$: 1710, 1730.

NMR spectrum (CCl$_4$( δ ppm: 3.70 (3H, singlet).

5.

1α-(2-Tetrahydropyranyloxy)-2β-hydroxymethyl-3α-(6-methoxycarbonylhexyl)-4α-(1,1'-ethylenedithioethyl)-cyclopentane (VIII)

A potassium salt of the starting compound prepared from 2.7 g of 1α-(2-tetrahydropyranyloxy)-2β-methoxycarbonyl-3α-(6-carboxyhexyl)-4α-(1,1'-ethylenedithioethyl)-cyclopentane and 1.3 g of potassium hydrogen carbonate was dissolved in 200 ml of anhydrous tetrahydrofuran. To this solution was added dropwise at room temperature 3.2 g of lithium boron hydride. After completion of the addition, the reaction mixture was stirred at room temperature for 15 hours and then at the reflux temperature for 5.5 hours. After completion of the reaction, the reaction mixture was poured into ice-water, acidified with dilute hydrochloric acid and acetic acid, and extracted with ether. The extract was washed with water and dried over anhydrous sodium sulfate. Then, the extract was subjected to esterification by the use of diazomethane. After completion of the reaction, the solvent was evaporated to leave the residue. The obtained residue was purified on a column of 41 g of neutral alumina (Woelm Co. product Grade III) and using benzene and a benzene solution containing 3% of ethyl acetate. The combined eluates were evaporated to remove the solvent, leaving 1.58 g of the desired compound as an oil.

IR spectrum (liquid film) $\nu_{max}$cm$^{-1}$: 1735, 3460.

NMR spectrum (CCl$_4$) δ ppm: 1.75 (3H, singlet), 3.59 (3H, singlet).

6.

1α-(2-Tetrahydropyranyloxy)-2β-hydroxymethyl-3α-(6-methoxycarbonylhexyl)-4α-acetylcyclopentane (IX)

In 300 ml of aqueous tetrahydrofuran (15%) were suspended 14.0 g of mercury (II) oxide and 9.2 g of a boron trifluoride — ethyl ether complex. To this suspension was added with stirring under ice-cooling 5.0 g of 1α-(2-tetrahydropyranyloxy)-2β-hydroxymethyl-3α-(6-methoxy-carbonylhexyl)-4α-(1,1'-ethylenedithioethyl)cyclopentane, and the mixture was stirred for 25 munutes. After completion of the reaction, ether was added to the reaction mixture, which was then filtered. The filtrate was washed with an aqueous sodium hydrogen carbonate solution and water, successively, and dried over anhydrous sodium sulfate. The solvent was then evaporated from the extract to leave the residue. The obtained residue was purified on a column of 100 g of alumina and using benzene and a benzene solution containing 1 – 40% ethyl acetate. The eluates were combined and evaporated to remove the solvent, leaving 3.421 g of the desired compound as an oil.

IR spectrum (liquid film) $\nu_{max}$cm$^{-1}$: 1705, 1738, 3450.

NMR spectrum (CCl$_4$) δ ppm: 1.12 (3H, singlet), 3.62 (3H, singlet).

7.

1α-(2-Tetrahydropyranyloxy)-2β-hydroxymethyl-3α-(6-methoxycarbonylhexyl)-4β-acetylcyclopentane (IX)

In 300 ml of 50% aqueous methanol containing 2.5% of potassium carbonate was dissolved 3.421 g of 1α-(2-tetrahydropyranyloxy)-2β-hydroxymethyl-3α-(6-methoxycarbonylhexyl)-4α-acetylcyclopentane prepared in Referential example 1-(6), and the solution was stirred at 50° C for 2.5 hours. After completion of the reaction, methanol was evaporated from the reaction mixture. The residual solution was, after acidified with acetic acid, extracted with ethyl acetate. The extract was dried over anhydrous sodium sulfate and evaporated to remove the solvent. The residue thus obtained was purified on a column of 30 g of alumina (Woelm Co. product Grade III) and using benzene and a benzene solution containing 1 – 40% of ethyl acetate. The eluates were combined and evaporated to remove the solvent, leaving 3.40 g of the desired compound as an oil.

IR spectrum (liquid film) $\nu_{max}$cm$^{-1}$: 1705, 1738, 3460.

NMR spectrum (CDCl$_3$) δ ppm: 1.14 (3H, singlet), 3.62 (3H, singlet).

8. 1α-(2-Tetrahydropyranyloxy)-2β-hydroxymethyl-3α-(6-methoxycarbonylhexyl)-4β-acetoxycyclopentane (X)

In 70 ml of dichloromethane was dissolved 3.2 g of 1α-(2-tetrahydropyranyloxy)-2β-hydroxymethyl-3α-(6-methoxycarbonylhexyl)-4β-acetylcyclopentane. To the solution were added 5.3 g of solid sodium hydrogen carbonate and 5.3 g of m-chloroperbenzoic acid, and the mixture was stirred at room temperature for 15 hours. After completion of the reaction, the reaction mixture was then treated in the same manner as in Referential example 1-(1) to give 1.658 g of the desired compound as an oil.

IR spectrum (liquid film) $\nu_{max}$cm$^{-1}$: 1740, 3470.

NMR spectrum (CCl$_4$) δ ppm: 1.98 (3H, singlet), 3.62 (3H, singlet).

9. 1α-(2-Tetrahydropyranyloxy)-2β-formyl-3α-(6-methoxycarbonylhexyl)-4β-acetoxycyclopentane (XI)

In 300 ml of dichloromethane was dissolved 1.753 g of 1α-(2-tetrahydropyranyloxy)-2β-hydroxymethyl-3α-(6-methoxycarbonylhexyl)-4β-acetoxycyclopentane. To this solution was added 17 g of a chromic anhydride pyridine complex, and the mixture was stirred under ice-cooling for 15 minutes. After completion of the reaction, to the reaction mixture were added successively ether and cooled dilute hydrochloric acid. The ethereal portion was washed with an aqueous sodium hydrogen carbonate solution and dried over anhydrous sodium sulfate. After drying, the reaction mixture was evaporated to remove the solvent, leaving 1.63 g of the desired compound as an oil.

IR spectrum (liquid film) $\nu_{max}$cm$^{-1}$: 1740, 2700.

NMR spectrum (CDCl$_3$) δ ppm: 1.93 (3H, singlet), 3.58 (3H, singlet), 9,69 (1H, broad doublet).

10. Dimethyl 2-oxo-4,8-dimethyl-7-nonenylphosphonate (XV)

41 ml of a hexane solution containing 15.1% of n-butyllithium was added dropwise with stirring at −60° C in a stream of argon to 80 ml of a tetrahydrofuran solutin containing 10.2 g of dimethyl methylphosphonate to prepare dimethyl methylphosphonate carbanion. To the carbanion thus obtained was added dropwise 30 ml of a tetrahydrofuran solution containing 7.227 g of methyl 3,7-dimethyl-6-octenoate with keeping the temperature below −50° C. The resulting mixture was then stirred at −50° − −60° C for 3 hours and 10 minutes, and, after removal of the cooling bath, the stirring was further continued until the inside temperature reached 0° C. After completion of the reaction, acetic acid and water were added successively to the reaction mixture and the mixture was then extracted with ether. The extract was washed with water, dried over anhydrous sodium sulfate, and evaporated to remove the solvent. The residual solution was distilled at 124° − 127° C/0.1 mmHg to give 4.858 g of the desired compound as an oil.

IR spectrum (liquid film) $\nu_{max}$cm$^{-1}$: 1715.

NMR spectrum (CCl$_4$) δ ppm: 0.90 (3H, doublet, J=6 Hz), 1.57 (3H, singlet), 1.64 (3H, singlet), 2.89 (2H, doublet, J=23 Hz), 3.66 (6H, doublet, J=11 Hz), 4.96 (1H, triplet, J=7 Hz).

11 Methyl 9β-acetoxy-11α-(2-tetrahydropyranyloxy)-15-oxo-17β-methyl-20-isopropylideneprost-13(trans)-enoate (XII)

292 g of 52.9% oily sodium hydride was washed with dry petroleum ether to remove the oil and suspended in 20 ml of dimethoxyethane. To this suspension was added dropwise with stirring under ice-cooling in a stream of argon 1.85 g of dimethyl 2-oxo-4,8-dimethyl-7-nonenylphosphonate in 20 ml of dimethoxyethane. After stirring for additional 3.5 hours, 10 ml of dimethoxyethane was added. To this solution was added dropwise under ice-cooling 2.35 g of 1α-(2-tetrahydropyranyloxy)-2β-formyl-3α-(6-methoxycarbonylhexyl)-4β-acetoxycyclopentane in 30 ml of dimethoxyethane, and the mixture was stirred for 25 minutes. After completion of the reaction, acetic acid and an excess amount of ether were successively added to the reaction mixture. The organic solvent portion was washed with water and dried over anhydrous sodium sulfate. The solvent was evaporated to leave 4.08 g of the residue. The obtained residue was purified on a column of alumina to give 2.018 g of the desired compound as an oil.

IR spectrum (liquid film) $\nu_{max}$cm$^{-1}$: 1740, 1695, 1670, 1630, 1035, 1025.

NMR spectrum (CCl$_4$) δ ppm: 0.90 (3H, doublet, J=6 Hz), 1.60 (3H, singlet), 1.64 (3H, singlet), 1.98 (3H, singlet), 3.59 (3H, singlet), 4.90 (2H, multiplet), 6.31 (2H, multiplet)

12. Methyl 9β-acetoxy-11α-(2-tetrahydropyranyloxy)-15-hydroxy-17β-methyl-20-isopropylideneprost-13(trans)-enoate (XIII)

1.5 g of sodium boron hydride in small portions was added under ice-cooling to 2.025 g of methyl 9β-acetoxy-11α-(2-tetrahydropyranyloxy)-15-oxo-17β-methyl-20-isopropyrideneprost-13(trans)-enoate in 50 ml of anhydrous methanol, and the mixture was stirred for 20 minutes. After completion of the reaction, acetic acid was added to decompose an excess of the sodium boron hydride. The mixture was, after addition of water, extracted with ethyl acetate. The extract was washed with water and dried over anhydrous sodium sulfate. The solvent was evaporated from the extract to leave 2.2 g of the residue. The obtained residue was then purified on a column of silica gel to give 1.989 g of the desired compound as an oil.

IR spectrum (liquid film) $\nu_{max}$ cm$^{-1}$: 3480, 1740.

NMR spectrum (CCl$_4$) δ ppm: 0.91 (3H, doublet, J=6 Hz), 1.57 (3H, singlet), 1.64 (3H, singlet), 1.95 (3H, singlet), 3.60 (3H, singlet), 5.49 (2H, multiplet).

13. Methyl 9β-acetoxy-11α,15α(or β)-dihydroxy-17β-methyl-20-isopropylideneprost-13(trans)-enoate (XIII)

In a mixture of acetic acid, water and tetrahydrofuran (40 ml, 17 ml and 8 ml, respectively) was dissolved 1.987 g of methyl 9β-acetoxy-11α-(2-tetrahydropyranyloxy)-15-hydroxy-17β-methyl-20-isopropylideneprost-13(trans)-enoate, and the solution was stirred at about 35° C for 4.5 hours. After completion of the reaction, water was added to the reaction mixture, and this was then extracted with ethyl acetate. The extract was washed with water and dried over anhydrous sodium sulfate. The solvent was evaporated from the extract to leave 2.11 g of the residue. The obtained residue was purified on a column of silica gel. Elution with a benzene solution containing 15 – 20% of ethyl acetate gave 418 mg of the 15β-hydroxy isomer of the desired compound. Elution with a benzene solution containing 20 – 30% of ethyl acetate gave 419 mg of a mixture of the isomers with respect to the 15 position. Further, elution with a benzene solution containing 30 – 80% of ethyl acetate gave 326 mg of the 15α-hydroxy isomer of the desired compound.

15α-Hydroxy isomer

IR spectrum (liquid film) $\nu_{max}$cm$^{-1}$: 3380, 1735.

NMR spectrum (CDCl$_3$) δ ppm: 0.91 (3H, doublet, J=6 Hz), 1.57 (3H, singlet), 1.64 (3H, singlet), 3.60 (3H, singlet), 4.95 (2H, multiplet), 5.45 (2H, multiplet).

15β-Hydroxy isomer

IR spectrum (liquid film) $\nu_{max}$cm$^{-1}$: 3430, 1735.

NMR spectrum (CDCl$_3$) δ ppm: 1.57 (3H, singlet), 1.68 (3H, singlet), 1.98 (3H, singlet), 3.63 (3H, singlet), 4.92 (2H, multiplet), 5.58 (2H, multiplet).

14. Methyl 9β-acetoxy-11α,15α-di(2-tetrahydropyranyloxy)-17β-methyl-20-isopropylideneprost-13(trans)-enoate (XIV)

5 ml of dihydropyran was added at room temperature to 510 mg of methyl 9β-acetoxy-11α, 15α-dihydroxy-17β-methyl-20-isopropylideneprost-13(trans)-enoate in 5 ml of benzene. The resulting mixture was, after addition of a catalytic amount of picric acid under ice-cooling, allowed to stand for 2.5 hours. After completion of the reaction, the reaction mixture was directly purified on a column of alumina to give 1.491 g of the desired compound as a crude oil.

IR spectrum (liquid film) $\nu_{max}$cm$^{-1}$: 1735, 1030, 1020.

NMR spectrum (CCl$_4$) δ ppm: 0.91 (3H, doublet, J=6 Hz), 1.93 (3H, singlet), 3.57 (3H, singlet), 5.43 (2H, multiplet).

15. Methyl 9β-acetoxy-11α, 15β-di(2-tetrahydropyranyloxy)17β-methyl-20-isopropylideneprost-13(trans)-enoate (XIV)

555 mg of methyl 9β-acetoxy-11α,15β-dihydroxy-17β-methyl-20-isopropylideneprost-13(trans)-enoate was reacted and treated in the same manner as in Referential example 1-(14) to give 1.30 g of a crude product of the desired compound.

IR spectrum (liquid film) $\nu_{max}$cm$^{-1}$: 1735, 1030, 1015.

NMR spectrum (CCl$_4$) β ppm: 0.89 (3H, doublet, J=6 Hz), 1.98 (3H, singlet), 3.58 (3H, singlet), 5.41 (2H, multiplet).

16. 9β-Hydroxy-11α,15α-di(2-tetrahydropyranyloxy)-17β-methyl-20-isopropylideneprost-13(trans)-enoic acid (II)

In a solution of 15 ml of water and 35 ml of methanol containing 1.5 g of potassium hydroxide was suspended 1.491 g of crude methyl 9β-acetoxy-11β,15β- di(2-tetrahydropyranyloxy)-17β-methyl-20-isopropylidene-prost-13(trans)-enoate, and the suspension was vigrously stirred at room temperature but with intermittent heating. 17 hours and 45 minutes later, water was added to the reaction mixture. The resulting mixture was then extracted with a hexane solution containing 50% of ether to remove the neutral materials, and subsequently the aqueous portion was, after acidification with acetic acid, extracted with ethyl acetate. The extract was washed with water and dried over anhydrous sodium sulfate. The solvent was then evaporated from the extract to leave 766 mg of the desired compound as an oil.

IR spectrum (liquid film) $\nu_{max}$cm$^{-1}$: 3400, 1710

NMR spectrum (CCl$_4$) δ ppm: 0.91 (3H, doublet, J=6 Hz), 5.03 (1H, triplet, J=6 Hz), 5.47 (2H, multiplet).

17. 9β-Hydroxy-11α,15β-di(2-tetrahydropyranyloxy)-17β-methyl-20-isopropylideneprost-13(trans)-enoic acid (II)

1.3 g of crude methyl 9β-acetoxy-11β,15α-di(2-tetrahydropyranyloxy)-17β-methyl-20-isopropylidene-prost-13(trans)-enoate was reacted and treated in the same manner as in Referential example 1-(16) to give 764 mg of the desired compound as an oil.

IR spectrum (liquid film) $\nu_{max}$cm$^{-1}$: 3400, 1710.

NMR spectrum (CCl$_4$) δ ppm: 0.84 (3H, doublet, J=6 Hz), 4.98 (1H, triplet, J=6 Hz), 5.38 (2H, multiplet).

Referential example 2

Methyl 9β-hydroxy-11α,15α-di(2-tetrahydropyranyloxy)-17β-methyl-20-isopropylideneprost-13(trans)-enoate (II)

Diazomethane in ether was added to 125 mg of 9β-hydroxy-11α,15α-di(2-tetrahydropyranyloxy)-17β-methyl-20-isopropylideneprost-13(trans)-enoic acid in 5 ml of ether until the reaction mixture turned pale yellow. After completion of the reaction, the solvent was evaporated under reduced pressure to leave 127 mg of the desired compound as an oil.

IR spectrum (liquid film) $\nu_{max}$cm$^{-1}$: 3400, 1730.

Referential example 3

9α-Hydroxy-11α, 15α (or β)-di(2-tetrahydropyranyloxy)-17β-methyl-20-isopropylideneprost-5(cis), 13(trans)-dienoic acid (II)

1. 3-Oxo-6-syn(3-oxo-5,9-dimethyldeca-1,8-dienyl)-7-antiacetoxy-2-oxabicyclo (3·3·0)-octane (XVII)

321 mg of 52.9% oily sodium hydride was washed with dry petroleum ether to remove the oil and suspended in 20 ml of dimethoxyethane. To the resulting solution was added dropwise with stirring under ice-cooling in a stream of argon 20 ml of a dimethoxyethane solution containing 2.035 g of dimethyl 2-oxo-4,8-dimethyl-7-nonenylphosphonate obtained in Referential example 1-(10). After stirring for 3 hours, 10 ml of dimethoxyethane was further added. To this solution was added dropwise under ice-cooling 1.35 g of 3-oxo-6-synformly-7-antiacetoxy-2-oxabicyclo-(3.3.0)-octane (XVI) in 30 ml of dimethoxyethane, and the mixture was stirred for additional 2 hours. After completion of the reaction, acetic acid and ether were successively added to the reaction mixture. The organic solvent portion was washed with water, dried over anhydrous sodium sulfate, and evaporated to remove the solvent. The obtained residue was purified on a column of silica gel to give 1.69 g of the desired compound as an oil.

IR spectrum (liquid film) $\nu_{max}$cm$^{-1}$: 1770, 1740, 1695, 1670, 1630.

NMR spectrum (CDCl$_3$) δ ppm: 0.90 (3H, doublet, J=6 Hz), 1.61 (3H, singlet), 1.65 (3H, singlet), 2.03 (3H, singlet).

2. 3-Oxo-6-syn(3α(or β)-hydroxy-5,9-dimethyldeca-1,8-dienyl)-7-antiacetoxy-2-oxabicyclo (3.3.0)-octane (XVIII)

0.8 ml of 0.55 M zinc boron hydride dimethoxymethane solution was added under ice-cooling to 270 mg of 3-oxo-6-syn(3-oxo-5,9-dimethyldeca-1,8-dienyl)-7-anti-acetoxy-2-oxabicyclo(3.3.0)-octane in 4 ml of dimethoxyethane, and the mixture was stirred for one hour. After completion of the reaction, acetic acid was added to the mixture so as to decompose an excess of the reagent, and the mixture was, after addition of water, extracted with ethyl acetate. The extract was washed with water, dried over anhydrous sodium sulfate and evaporated to remove the solvent. The obtained residue was subjected to preparative thin layer chromatography and purified by developing with ether. There was obtained 89 mg of the 3α-isomer of the desired compound from the less polar portion and 80 mg of the 3β-isomer of the desired compound from the more polar portion.

3α-Hydroxy isomer

IR spectrum (liquid film) $\nu_{max}$cm$^{-1}$: 3500, 1780.

NMR spectrum (CDCl$_3$) δ ppm: 0.91 (3H, doublet, J=6 Hz), 1.58 (3H, singlet), 1.65 (3H, singlet), 5.51 (2H, multiplet).

3β-Hydroxy isomer

IR spectrum (liquid film) $\nu_{max}$cm$^{-1}$: 3500, 1780.

NMR spectrum (CDCl$_3$) δ ppm: 0.90 (3H, doublet, J=6 Hz), 1.57 (3H, singlet), 1.64 (3H, singlet), 5.51 (2H, multiplet).

3. 3-Oxo-6-syn(3α-hydroxy-5,9-dimethyldeca-1,8-dienyl)-7-antihydroxy-2-oxabicyclo (3.3.0)-octane (XVIII)

In 2 ml of anhydrous methanol was dissolved 120 mg of 3-oxo-6-syn(3α-hydroxy-5,9-dimethyldeca-1,8-dienyl)-7-antiacetoxy-2-oxabicyclo (3.3.0)-octane, and the solution was, after addition of 65 mg of anhydrous potassium carbonate, stirred for 20 minutes. After completion of the reaction, acetic acid and water were successively added to the mixture, and this was then extracted with ethyl acetate. The extract was washed with water and dried over anhydrous sodium sulfate. The solvent was evaporated from the extract to leave 93 mg of the desired compound as an oil.

IR spectrum (liquid film) $\nu_{max}$cm$^{-1}$: 1770.

NMR spectrum (CDCl$_3$) δ ppm: 0.91 (3H, doublet, J=6 Hz), 1.58 (3H, singlet), 1.68 (3H, singlet), 5.54 (2H, multiplet).

4. 3-Oxo-6-syn(3β-hydroxy-5,9-dimethyldeca-1,8-dienyl)-7-antihydroxy-2-oxabicyclo (3.3.0)-octane (XVIII)

3-Oxo-6-syn(3β-hydroxy-5,9-dimethyldeca-1,8-dienyl)-7-antiacetoxy-2-oxabicyclo (3.3.0)-octane was reacted and treated in the same manner as in Referential example 3-(3) to give the desired compound as an oil.

IR spectrum (liquid film) $\nu_{max}$cm$^{-1}$: 1770.

NMR spectrum (CDCl$_3$) δ ppm: 0.90 (3H, doublet, J=6 Hz), 1.57 (3H, singlet), 1.68 (3H, singlet), 5.54 (2H, multiplet).

5. 3-Oxo-6-syn(3α-(2-tetrahydropyranyloxy)-5,9-dimethyldeca-1,8-dienyl)-7-anti(2-tetrahydropyranyloxy)-2-oxabicyclo (3.3.0)-octane (XIX)

150 mg of 3-oxo-6-syn(3α-hydroxy-5,9-dimethyldeca-1,8-dienyl)-7-antihydroxy-2-oxabicyclo (3.3.0)-octane was reacted and treated in the same manner as in Referential example 1–(14) to give 301 mg of a crude product of the desired compound.

IR spectrum (liquid film) $\nu_{max}$cm$^{-1}$: 1770, 1030.

NMR spectrum (CDCl$_3$) δ ppm: 0.91 (3H, doublet, J=6 Hz).

6. 3-Oxo-6-syn(3β-(2-tetrahydropyranyloxy)-5,9-dimethyldeca-1,8-dienyl)-7-anti(2-tetrahydropyranyloxy)-2-oxabicyclo (3.3.)-octane (XIX)

3-Oxo-6-syn(3α-hydroxy-5,9-dimethyldeca-1,8-dienyl)-7-antihydroxy-2-oxabicyclo (3.3.0)-octane was reacted and treated in the same manner as in Referential example 1–(14) to give a crude product of the desired compound.

IR spectrum (liquid film) $\nu_{max}$cm$^{-1}$: 1770, 1025.

NMR spectrum (CDCl$_3$) δ ppm: 0.90 (3H, doublet, J=6 Hz).

7. 3-Hydroxy-6-syn(3α-(2-tetrahydropyranyloxy)-5,9-dimethyldeca-1,8-dienyl)-7-anti(2-tetrahydropyranyloxy)-2-oxabicyclo (3.3.0)-octane (XX)

In 5 ml of toluene was dissolved 190 mg of 3-oxo-6-syn(3α-(2-tetrahydropyranyloxy)-5,9-dimethyldeca-1,8-dienyl)-7-anti(2-tetrahydropyranyloxy)-2-oxabicyclo-(3.3.0)-octane, and the solution was cooled to −60° C. To this solution was added with stirring 190 mg of diisobutylaluminum hydride in 1 ml of toluene, and the mixture was stirred for 30 minutes. After completion of the reaction 1 ml of methanol and water were added to the reaction mixture, and this was extracted with ethyl acetate. The extract was washed with water and dried over anhydrous sodium sulfate. The solvent was evaporated from the extract to leave 170 mg of the desired compound as an oil.

IR spectrum (liquid film) $\nu_{max}$cm$^{-1}$: 3420, 1030.

NMR spectrum (CDCl$_3$) δ ppm: 0.91 (3H, doublet, J=6 Hz).

8. 3-Hydroxy-6-syn(3β-(2-tetrahydropyranyloxy)-5,9-dimethyldeca-1,8-dienyl)-7-anti(2-tetrahydropyranyloxy)-2-oxabicyclo (3.3.0)-octane (XX)

3-Oxo-6-syn(3β-(2-tetrahydropyranyloxy)-5,9-dimethyldeca-1,8-dienyl)-7-anti(2-tetrahydropyranyloxy)-2-oxabicyclo(3.3.0)-octane was reacted and treated in the same manner as in Referential example 3-(7) to give the desired compound as an oil.

IR spectrum (liquid film) $\nu_{max}$cm$^{-1}$: 3410, 1030.

NMR spectrum (CDCl$_3$) δ ppm: 0.90 (3H, doublet, J=6 Hz)

9. 9α-Hydroxy-11α,15α-di(2-tetrahydropyranyloxy)-17β-methyl-20-isopropylideneprost-5(cis),13(trans)-dienoic acid (II)

624 mg of triphenylcarboxybutylphosphonium bromide in 2 ml of dimethylsulfoxide was added dropwise with stirring below −20° C in a stream of argon to 1.3 ml of 2M sodium methylsulfinyl carbanion in dimethylsulfoxide so that a ylide solution having red color was obtained. To this solution was added 220 mg of 3-hydroxy-6-syn(3α-(2-tetrahydropyranyloxy)-5,9-dimethyldeca-1,8-dienyl)-7-anti(2-tetrahydropyranyloxy)-2-oxabicyclo(3·3·0)-octane in 5 ml of dimethylsulfoxide, and the mixture was stirred at room temperature for 20 hours. After completion of the reaction, the dimethylsulfoxide was evaporated under reduced pressure to leave the residue. An aqueous sodium hydrogen carbonate solution was added to the obtained residue, and the mixture was then washed with ethyl acetate to remove the neutral materials. The aqueous portion was adjusted to about pH 3 with oxalic acid and extracted with a mixture of hexane - ether (1 : 1). The extract was washed with water and dried over anhydrous sodium sulfate. The solvent was evaporated from the extract to leave 198 mg of the desired compound as an oil.

IR spectrum (liquid film) $\nu_{max}$cm$^{-1}$: 3400, 1708.

NMR spectrum (CCl$_4$) δ ppm: 0.91(3H, doublet, J=6 Hz), 5.01 (1H, triplet, J=6 Hz).

9α-Hydroxy-11α,15β-di(2-tetrahydropyranyloxy)-17β-methyl-20-isopropylideneprost-5(cis),13(trans)-dienoic acid (II)

3-Hydroxy-6-syn(3β-(2-tetrahydropyranyloxy)-5,9-dimethyldeca-1,8-dienyl)-7-anti(2-tetrahydropyranyloxy)-2-oxabicyclo [3·3·0]-octane was reacted and treated in the same manner as in Referential example 3-(9) to give the desired compound as an oil.

IR spectrum (liquid film) $\nu_{max}$ cm$^{-1}$: 3400, 1710.

NMR spectrum (CCl$_4$) δ ppm: 0.91 (3H, doublet, J32 6 Hz), 5.02 (1H, triplet, J=6 Hz).

Referential example 4

Methyl 9α-hydroxy-11α, 15α-di(2-tetrahydropyranyloxy)-17β-methyl-20-isopropylideneprost-5(cis), 13(trans)-dienoate (II)

An ethereal solution of diazomethane was added to 730 mg of 9α-hydroxy-11α, 15α-di(2-tetrahydropyranyloxy)-17β-methyl-20-isopropylideneprost-5(cis), 13(trans)-dienoic acid in 5 ml of ether until the reaction mixture turned pale yellow. After completion of the reaction, the solvent was evaporated under reduced pressure to give 728 mg of the desired compound as an oil.

IR spectrum (liquid film) $\nu_{max}$cm$^{-1}$: 3400, 1730.

NMR spectrum (CCl$_4$) δ ppm: 0.91 (3H, doublet, J=6 Hz), 5.01 (1H, triplet, J=6 Hz).

Referential example 5

9β-Hydroxy-11α, 15-di(2-tetrahydropyranyloxy)-20-isopropylideneprost-13(trans)-enoic acid 1.
9β-Acetoxy-11α-(2-tetrahydropyranyloxy)-15-oxo-20-isopropylideneprost-13(trans)-enoic acid (XII)

117.4 mg of 52.9% oily sodium hydride, 1 g of dimethyl 2-oxo-8-methyl-7-nonenylphosphonate prepared by the procedure state in Referential example 1-(10) and 680 mg of 1α-(2-tetrahydropyranyloxy)-2β-formyl-3α-(6-methoxycarbonylhexyl)-4β-acetoxycyclopentane were reacted and treated in the same manner as in Referential example 1-(11) to give 898 mg of the desired compound as an oil.

IR spectrum (liquid film) $\nu_{max}$cm$^{-1}$: 1735, 1695, 1670, 1625, 1035.

NMR spectrum (CCl$_4$) δ ppm: 1.48 (3H, singlet), 1.58 (3H, singlet), 1.87 (3H, singlet), 3.48 (3H, singlet), 6.22 (2H, multiplet).

2. Methyl 9β-acetoxy-11α-(2-tetrahydropyranyloxy)-15-hydroxy-20-isopropylideneprost-13(trans)-enoate (XIII)

898 mg of methly 9β-acetoxy-11β-(2-tetrahydropyranyloxy)-15-oxo-20-isopropylideneprost-13(trans)-enoate was reacted and treated in the same manner as in Referential example 1-(12) to give 851 mg of the desired compound as an oil.

IR spectrum (liquid film) $\nu_{max}$cm$^{-1}$: 3420, 1735.

3. Methyl 9β-acetoxy-11α, 15-di(2-tetrahydropyranyloxy)-20-isopropylideneprost-13(trans)-enoate (XIV)

851 mg of Methyl 9β-acetoxy-11α-(2-tetrahydropyranyloxy)-15-hydroxy-20-isopropylideneprost-13(trans)-enoate was reacted and treated in the same manner as in Referential example 1-(14) to give 1.55 g of a crude product of the desired compound.

4.
9β-Hydroxy-11α,15-di(2-tetrahydropyranyloxy)-20-isopropylideneprost-13(trans)-enoic acid (II)

1.55 g of crude methyl 9β-acetoxy-11α,15-di(2-tetrahydropyranyloxy)-20-isopropylideneprost-13(trans)-enoate was reacted and treated in the same manner as in Referential example 1-(16) to give 1.01 g of the desired compound as an oil.

IR spectrum (liquid film) $\nu_{max}$cm$^{-1}$: 3380, 1710, 1035, 1020.

NMR spectrum (CCl$_4$) δ ppm: 5.44 (2H, multiplet).

Referential example 6

9α-Hydroxy-11α,15α(or β)-di(2-tetrahydropyranyloxy)-20-isopropylideneprost-5(cis), 13(trans)-dienoic acid (II)

1.
3-Oxo-6-syn(3-oxo-9-methyldeca-1,8-dienyl)-7-anti(p-phenylbenzoyloxy)-2-oxa-cis-bicylco-[3·3·0]-octane (XVII)

346 mg of 52.9% oily sodium hydride was washed with dry petroleum ether to remove the oil and suspended in 20 ml of dimethoxyethane. To the suspension was added dropwise under ice-cooling in a stream of argon 20 ml of dimethoxyethane solution containing 2.075 g of dimethyl 2-oxo-8-methyl-7-nonenylphosphonate obtained in Referential example 5-(1), followed by stirring for additional 3.5 hours. To the suspension was added 10 ml of dimethoxyethane and added dropwise under ice-cooling 30 ml of dimethoxyethane solution containing 1.22 g of 3-oxo-6-synformyl-7-anti(p-phenylbenzoyloxy)-2-oxa-cis-bicyclo-[3·3·0]-octane (XVI). The mixture was stirred for 2 hours. After completion of the reaction, the mixture was treated with the same procedure as in Referential example 3-(1) to give 1.37 g of the desired product as an oil.

IR spectrum (liquid film) $\nu_{max}$cm$^{-1}$: 1783, 1723, 1680, 1635, 1280, 1185, 1120, 755.

NMR spectrum (CDCl$_3$) δ ppm: 5.0-5.5 (3H, multiplet), 6.28 (1H, doublet), 6.8 (1H, quartette), 7.3-8.2 (9H, multiplet)

2. 3-Oxo-6-syn[3β(or 3β)-hydroxy-9-methyl-1,8-dienyl]-7-anti (p-phenylbenzoyloxy)-2-oxa-cis-bicyclo [3·3·0]-octane (XVIII)

In 5 ml of dimethoxyethane was dissolved 290 mg of 3-oxo-6-syn (3-oxo-9 methyldeca-1,8-dienyl)-7-anti(p-phenylbenzoyloxy)-2-oxa-cis-bicyclo [3·3·0]-octane. To the solution was added under ice-cooling 1 ml of 0.55 molar concentration zinc boron hydride dimethoxyethane solution, followed by stirring for one hour. After completion of the reaction, the mixture was treated with the same procedure as in Referential example 3–(2). The product obtained was subjected to a preparative thin layer chromatography and developed with ether to give 95 mg of the 3α-isomer of the desired product from the less polar portion and 77 mg of the 3β-isomer of the desired product from the more polar portion.

3α-Hydroxy isomer

IR spectrum (liquid film) $\nu_{max}$cm$^{-1}$: 3500, 1780, 1720, 1615, 1280, 1185, 1120 975, 750

NMR spectrum (CDCl$_3$) δ ppm: 4.13 (1H, multiplet), 4.9–5.4 (3H, multiplet), 5.64 (2H, multiplet), 7.3–8.2 (9H, multiplet)

3β-Hydroxy isomer

IR spectrum (liquid film) $\nu_{max}$cm$^{-1}$: 3500, 1780, 1720, 1615, 1280, 1185, 1120, 975, 750.

NMR spectrum (CDCl$_3$) δ ppm:

4.13 (1H, multiplet), 4.9–5.4 (3H, multiplet), 5.64 (2H, multiplet), 7.3–8.2 (9H, multiplet)

3. 3-Oxo-6-syn(3α-hydroxy-9-methyldeca-1,8-dienyl)-7-antihydroxy-2-oxa-cis-bicyclo [3·3·0]-octane (XVIII)

In 3 ml of anhydrous methanol were dissolved 140 mg of 3-oxo-6-syn(3α-hydroxy-9-methyldeca-1,8-dienyl)-7-anti(p-phenylbenzoyloxy)-2-oxa-cis-bicyclo[-3·3·0]-octane and 75 mg of anhydrous potassium carbonate, followed by stirring for 35 minutes. After completion of the reaction, the mixture was treated by the same procedure as in Referential example 3-(3) to give 99 mg of the desired product as an oil.

IR spectrum (liquid film) $\nu_{max}$cm$^{-1}$: 3400, 1760, 1175, 1080, 970.

NMR spectrum (CDCl$_3$) δ ppm: 1.60 (6H, doublet), 3.8–4.2 (2H, multiplet), 4.8–5.3 (2H, multiplet), 5.55 (2H, multiplet).

4. 3-Oxo-6-syn(3β-hydroxy-9-methyl-deca-1,8-dienyl)-7-antihydroxy-2oxa-cis-bicyclo [3·3·0]-octane (XVIII)

Following the same precedure as in Referential example 6-(3), but replacing 3-oxo-6-syn(3α-hydroxy-9-methyldeca-1,8-dienyl)-7-anti(p-phenylbenzoyloxy)-2-oxa-cis-bicyclo [3·3·0]-octane with 91 mg of 3-oxo-6-syn(3β-hydroxy-9 -methyldeca-1,8-dienyl)-7-anti-(p-phenylbenzoyloxy)-2-oxa-cis-bicyclo [3·3·0]-octane, there was obtained the desired product.

IR spectrum (liquid film) $\nu_{max}$cm$^{-1}$: 3400, 1760, 1175, 1080, 970.

NMR spectrum (CDCl$_3$) δ ppm: 1.6 (6H, doublet), 3.8–4.2 (2H, multiplet), 4.8–5.3 (2H, multiplet), 5.55 (2H, multiplet).

5. 3-Oxo-6-syn[3α-(2-tetrahydropyranyloxy)-9-methyl-deca-1,8-dienyl]-7 -anti(2-tetrahydropyranyloxy)-2-oxa-cis-bicyclo [3·3·0]-octane (XIX)

To 15 ml of benzene solution of containing 3.08 g of 3-oxo-6-syn(3β-hydroxy-9-methyldeca-1,8-dienyl)-7-antihydroxy-2-oxa-cis-bicyclo [3·3·0]-octane was added 1.85 g dihydropyrane at room temperature and added a catalytic amount of picric acid under ice-cooling, followed by allowing for 3 hours. After completion of the reaction, 200 ml of ether was added to the reaction mixture. The mixture was neutralized with 10% aqueous sodium bicarbonate, washed with water and dried over anhydrous sodium sulfate. The solvent was distilled off and the residue was purified by silica gel column chromatograpy to give 4.3 g of the desired product as an oil.

IR spectrum (liquid film) $\nu_{max}$cm$^{-1}$: 1775, 1130, 1070, 1015, 970.

NMR spectrum (CDCl$_3$) δ ppm: 4.7 (2H, multiplet), 4.8–5.2 (2H, multiplet), 5.0 (2H, multiplet)

6. 3-Oxo-6-syn[3β-(2-tetrahydropyranyloxy)-9-methyl-deca-1,8-dienyl]-7-anti(2-tetrahydropyranyloxy)-2-oxa-cis-bicyclo [3·3·0]-octane (XIX)

Following the same procedure as in Referential example 6-(5), but replacing 3-oxo-6-syn(3α-hydroxy-9-methyldeca-1,8-dienyl)-7-antihydroxy-2-oxa-cis-bicyclo- [3·3·0]-octane with 2,7g of 3-oxo-6-syn(3β-hydroxy-9-methyldeca-1,8-dienyl)-7-antihydroxy-2-oxa-cis-bicyclo-[3·3·0]-octane, there was obtained 3.5 g of the desired product as an oil.

IR spectrum (liquid film) $\nu_{max}$cm$^{-1}$: 1775, 1130, 1070, 1015, 970.

NMR spectrum (CDCl$_3$) δ ppm: 4.7 (2H, multiplet), 4.8–5.2 (2H, multiplet), 5.0 (2H, multiplet).

7. 3-Hydroxy-6-syn[3α-(2-tetrahydropyranyloxy)-9-methyldeca-1,8-dienyl]-7-anti(2-tetrahydropyranyloxy)-2-oxa-cis-bicyclo [3·3·3-octane (XX)

Following the same procedure as in Referential example 3-(7), but replacing 3-oxo-6-syn[3α-(2-tetrahydropyranyloxy)-5,9-dimethyldeca-1,8-dienyl]-7-anti(2-tetrahydropyranyloxy)-2-oxa-cis-bicyclo [3·3·3]-octane with 4.3 g of 3-oxo-6-syn [3α-(2-tetrahydropyranyloxy)-9-methyldeca-1,8-dienyl]-7-anti(2-tetrahydropyranyloxy)-2-oxa-cis-bicyclo [3·3·0]-octane, there was obtained 4.1 g of the desired product as an oil.

IR spectrum (liquid film) $\nu_{max}$cm$^{-1}$: 3400, 1130, 1070, 1015, 970

NMR spectrum (CDCl$_3$) δ ppm: 4.7 (2H, multiplet), 5.15 (1H, triplet), 5.6 (2H, multiplet)

8. 3-Hydroxy-6-syn[3α(2-tetrahydropyranyloxy)-9-methyldeca-1,8-dienyl]-7-anti(2-tetrahydropyranyloxy)-2-oxa-cis-bicyclo [3·3·0]-octane (XX)

Following the same procedure as in Referential example 3-(7), but replacing 3-oxo-6-syn[3α-(2-tetrahydropyranyloxy)-5,9-dimethyldeca-1,8-dienyl]-7-anti-(2-tetrahydropyranyloxy)-2-oxa-cis-bicyclo [3·3·0]-octane with 3.5 g of 3-oxo-6-syn[3β-(2-tetrahydropyranyloxy)-9-methyldeca-1,8-dienyl]-7-anti(2-tetrahydropyranyloxy)-2-oxa-cis-bicyclo [3·3·0]-octane, there was obtained 3.3. g of the desired product as an oil.

IR spectrum (liquid film) $v_{max}$cm$^{-1}$: 3400, 1130, 1070, 1015, 970.

NMR spectrum (CDCl$_3$) δ ppm: 4.7 (2H, multiplet), 5.15 (1H, triplet), 5.6 (2H, multiplet).

9.

9α-Hydroxy-11α,15α-di(2-tetrahydropyranyloxy)-20-isopropylideneprost-5(cis), 13(trans)-dienoic acid (II)

Following the same procedure as in Referential example 3-(9), but replacing 3-hydroxy-6-syn[3α-(2-tetrahydropyranyloxy)-5,9 -dimethyldeca-1,8 -dienyl]-7-anti(2-tetrahydropyranyloxy)-2-oxa-bicyclo [3·3·0]-octane with 4.1 g of 3-hydroxy-6syn[3α-(2-tetrahydropyranyloxy)-9-methyldeca-1,8-dienyl]-7-anti(2-tetrahydropyranyloxy)-2-oxa-cis-bicyclo [3·3·0]-octane, there was obtained 3.6 g of the desired product as an oil.

IR spectrum (liquid film) $v_{max}$cm$^{-1}$: 3450, 3200, 2750, 1715, 1160, 1105, 1020.

NMR spectrum (CDCl$_3$) δ ppm: 4.73 (2H, multiplet), 5.17 (1H, triplet), 5.5 (4H, multiplet).

10.

9α-Hydroxy-11α,15β-di(2-tetrahydropyranyloxy)-20-isopropylideneprost-5(cis), 13(trans)-dienoic acid (II)

Following the same procedure as in Referential example 3-(9), but replacing 3-oxo-6-syn(3α-(2-tetrahydropyranyloxy)-5,9-dimethyldeca-1,8-dienyl)-7-anti(2-tetrahydropyranyloxy)-2-oxa-cis-bicyclo (3·3·0)-octane with 3.3 g of 3-hydroxy-6-syn(3β-(2-tetrahydropyranyloxy)-9-methyldeca-1,8-dienyl)-7-anti(2-tetrahydropyranyloxy)-2-oxa-cis-bicyclo (3·3·0)-octane, there was obtained 3.0 g of the desired product as an oil.

IR spectrum (liquid film) $v_{max}$cm$^{-1}$: 3450, 3200, 2750, 1715, 1160, 1105, 1020.

NMR spectrum (CDCl$_3$) δppm: 4.73 (2H, multiplet), 5.17 (1H, triplet), 5.5 (4H, multiplet).

Referential example 7

9α-Hydroxy-15-(2-tetrahydropyranyloxy)-20-isopropylideneprost-13(trans)-enoic acid (II)

1.

3-Oxo-6-syn(2-tetrahydropyranyloxymethyl)-2-oxabicyclo (3·3·0)-octane (XXIII)

In 15 ml of anhydrous 2,3-dihydropyran was dissolved 3.35 g of 3-oxo-6-synhydroxymethyl-2-oxa-bicyclo (3·3·0)-octane, and, after addition of 15 mg of p-toluenesulfonic acid, the resulting solution was stirred at room temperature for 20 minutes. After completion of the reaction, the solution was diluted with 200 ml of ethyl acetate and washed with three portions of 100 ml of a saturated aqueous doium chlorid solution. After drying it over anhydrous sodium sulfate, the solvent was evaporated to leave 5.95 g of the desired compound as an oil.

IR spectrum (liquid film) $v_{max}$cm$^{-1}$: 1780, 1165, 1125, 1035.

2.

3-Hydroxy-6syn(2-tetrahydropyranyloxymethyl)-2-oxa-bicyclo (3·3·0)-octane (XXIV)

In 100 ml of anhydrous toluene was dissolved 5.9 g of 3-oxo-6syn(2-tetrahydropyranyloxymethyl)-2-oxa-bicyclo (3·3·0)-octane obtained in Referential example 7-(1), and the solution was then stirred at −70° C in the stream of argon. To this solution was slowly added 21 ml of a diisobutylaluminum hydride solution (25 g/100 ml of n-hexane), and the solution was stirred at −70° C for 30 minutes. After completion of the reaction, to the solution was added slowly 180 ml of a mixture of tetrahydrofuran and water (2:1). After the temperature of the resulting mixture reached room temperature, the precipitated insoluble substance was filtered off over Celite. The filtrate was diluted with a saturated aqueous sodium chloride solution and extracted with ethyl acetate. The organic portion was then washed with water and dried over anhydrous sodium sulfate. Upon evaporation of the solvent, there was obtained 5.89 g of the desired compound as an oil.

IR spectrum (liqiud film) $v_{max}$cm$^{-1}$: 3450, 1125, 1065, 1024.

NMR spectrum (CDCl$_3$) δ ppm: 4.6-4.8 (2H, multiplet), 5.58 (1H, multiplet).

3.

1α-Hydroxy-2α-(6-methoxycarbonyl-2-cis-hexenyl)-3β-(2-tetrahydropyranyloxymethyl)-cyclopentane (XXV)

To a sodium methylsulfonylcarbonion solution prepared from 7.10 g of sodium hydride containing 50% of an oil and 200 ml of dimethylsulfoxide was added, below a temperature of −20° C in a stream of argon, 32 g of triphenylphosphonium bromide, to prepare a red color ylide solution. To this solution was added 20 ml of dimethylsulfoxide containing 5.8 g of 3-hydroxy-6-syn(2-tetrahydroyranyloxymethyl)-2-oxa-bicyclo(3·•3·0)-octane, and the mixture was stirred at room temperature for 30 minutes. After completion of the reaction, the reaction mixture was diluted with 500 ml of cold (0° C) 15% aqueous hydrochloric acid and extracted with ether. The extract was washed with water and dried over anhydrous sodium sulfate. The solvent was evaporated to leave an oily residue of the carboxylic acid.

The obtained residue was treated with an ethereal solution of diazomethane. Upon evaporation of the ether, 14 g of the ester was obtained as a residue. The residue was treated with column chromatography using 140 g of silica gel to give 6.57 g of the desired compound as an oil.

IR spectrum (liquid film) $v_{max}$cm$^{-1}$: 3480, 1740, 1200, 1140, 1120, 1030.

NMR spectrum (CDCl$_3$) δ ppm: 3.67 (3H, singlet), 4.23 (1H, multiplet) 4.80 (1H, multiplet), 5.50 (2H, multiplet).

4.

1α-Acetoxy-2α-(6-methoxycarbonyl)-2-cis-hexeneyl-3β-(2-tetrahydropyranyloxymethyl)-cyclopentane (XXVI)

In a mixture of 20 ml of pyridine and 10 ml of acetic anhydride was dissolved 6.49 g of 1α-hydroxy-2α-(6-methoxycarbonyl-2-cis-hexenyl)-3β-(2-tetrahydropyranyloxymethyl)-cyclopentane, and the resulting solution was stirred at 40° C for 2 hours. After completion of the reaction, the reaction mixture was diluted with 150 ml of water and extracted with a mixture of benzene and ethyl acetate.

The extract was then washed with water and dried over anhydrous sodium sulfate. The solvent was evaporated under reduced pressure to leave 7.26 g of the desired compound as an oil.

IR spectrum (liquid film) $v_{max}$cm$^{-1}$: 1740, 1245, 1030.

NMR spectrum (CDCl$_3$) δ ppm: 2.03 (3H, singlet), 3.67 (3H, singlet), 4.62 (1H, multiplet), 5.23 (1H, multiplet), 5.42 (2H, multiplet).

5. 1α-Acetoxy-2α-(6-methoxycarbonyl-2-cis-hexenyl)-3α-hydroxymethyl-cyclopentane (XXVII)

In 150 ml of aqueous methanol containing water (10%) was dissolved 7.20 g of 1α-acetoxy-2α-(6-methoxy-carbonyl-2-cis-hexenyl)-3α-(2-tetrahydropyranyloxymethyl)cyclopentane, and, after addition of 1.4 g of p-toluenesulfonic acid, the mixture was stirred at 40° C for one hour. After completion of the reaction, the mixture was diluted with 400 ml of ether and washed with a saturated aqueous sodium chloride solution to remove the acid. After drying it over anhydrous sodium sulfate, the solvent was evaporated under reduced pressure to leave 5.79 g of an oily residue. The obtained residue was treated with column chromatography using 80 g of silica gel to give 5.053 g of the desired compound as an oil.

IR spectrum (liquid film) $v_{max}$cm$^{-1}$: 3500, 1740, 1380, 1250, 1170, 1025

NMR spectrum (CDCl$_3$) δ ppm: 2.03 (3H, singlet), 3.65 (2H, multiplet), 3.68 (3H, singlet), 5.25 (1H, multiplet), 5.45 (2H, multiplet).

6. 1α-Acetoxy-2α(6-methoxycarbonylhexyl)-3β-hydroxymethyl-cyclopentane (XXVIII)

In 50 ml of methanol was dissolved 3.0 g of 1α-acetoxy-2α-(6-methoxycarbonyl-2-cis-hexenyl)-3α-hydroxymethyl-cyclpentane, and the resulting solution was subjected to the usual hydrogenation using 2.0 g of 5% palladium - carbon catalyst. After filtering off the catalyst, the solvent was evaporated under reduced pressure to leave 2.8 g of the desired compound as an oil.

IR spectrum (liquid film) $v_{max}$cm$^{-1}$: 3500, 1740, 1380, 1250, 1175, 1020.

NMR spectrum (CDCl$_3$) δ ppm: 2.03 (3H, singlet), 3.63 (2H, multiplet), 3.70 (3H, singlet), 5.28 (1H, multiplet).

7. 1β-Acetoxy-2β-(6-methoxycarbonylhexyl)-3β-formyl-cyclopentane (XXIX)

To a mixture of 200 ml of anhydrous dischlormethane and 11.7 g of pyridine was added with stirring at 15° C in a stream of argon, 7.36 g of chromic anhydride, to prepare Collins oxidizing reagent. The obtained solution was cooled to 3°- 5° C, and 2.76 g of 1α-acetoxy-2α-(6-methoxycarbonylhexyl)-3β-hydroxymethyl-cyclopentane was added thereto. The mixture was then stirred for 20 minutes. After completion of the reaction, the reaction mixture was diluted with 1 liter of ether. The mixture was then washed with 3% aqueous sodium hydroxide solution, 3% hydrochloric acid, 5% aqueous sodium hydrogen carbonate solution and water, successively, and dried over anhydrous sodium sulfate. The solvent was evaporated to give 2.56 g of the desired compound as an oil.

8. Methyl 9α-acetoxy-15-oxo-20-isopropylideneprost-13(trans)-enoate (XXX)

0.495 g of 50% oily sodium hydride was washed with dry petroleum ether to remove the oil. The obtained sodium hydride was suspended in 150 ml of anhydrous dimethoxyethane, and under ice-cooling, to this suspension was added dropwise with stirring in a stream of argon, 2.7 g of dimethyl-2-oxo-8-methyl-7-nonenylphosphonate. The mixture was then stirred at room temperature for 4 hours. To the resulting solution was added under ice-cooling 2.50 g of 1α-acetoxy-2α-(6-methoxycarbonylhexyl)-3β-formyl-cyclopentane, and the mixture was stirred for 2 hours. After completion of the reaction, 200 ml of ether was added to the resulting solution. The organic solution was washed with dilute hydrochloric acid and water, successively, and dried over anhydrous sodium sulfate. The organic solvent was evaporated under reduced pressure to leave 4.58 g of an oily residue. The obtained residue was purified on alumina column to give 2.45 g of the desired compound as an oil.

IR spectrum (liquid film) $v_{max}$cm$^{-1}$: 1740, 1700, 1670, 1625, 1370, 1240, 1170, 1020.

NMR spectrum (CDCl$_3$) δ ppm: 2.03 (3H, singlet), 3.64 (3H, singlet), 5.00 – 5.35 (2H, multiplet), 6.10 (1H, doublet), 6.52 (1H, quarttet).

9. Methyl 9α-acetoxy-15-hydroxy-20-isopropylideneprost-13(trans)-enoate (XXXI)

In 50 ml of anhydrous methanol was dissolved 2.4 g of methyl 9α-acetoxy-15-oxo-20-isopropylideneprost-13-(trans)-enoate, and the solution was cooled to 3°– 5° C and stirred. To this solution was added 210 mg of sodium boron hydride, and the mixture was stirred at 3°– 5° C for one hour. After completion of the reaction, the mixture was diluted with cold 3% aqueous hydrochloric acid and extracted with a mixture of benzene and ethyl acetate. The extract was washed with water and dried over anhydrous sodium sulfate. The solvent was evaporate to leave 2.5 g of an oily residue. The obtained residue was purified on silica gel column to give 2.36 g of the desired compound as an oil.

IR spectrum (liquid film) $v_{max}$cm$^{-1}$: 3500, 1740, 1245, 1020.

NMR spectrum (CDCl$_3$) δ ppm: 2.0 (3H, singlet), 3.65 (3H, singlet), 4.07 (1H, multiplet,) 5.0 – 5.4 (2H, multiplet), 5.50 (2H, multiplet).

10. Methyl 9α-acetoxy-15-(2-tetrahydropyranyoxy)-20-isopropylideneprost-13(trans-enoate (XXXII)

In 5 ml of 2,3-dihydropyran was dissolved 2.3 g of methyl 9α-acetoxy-15-hydroxy-20-isopropylideneprost-13(trans)-enoate, and, after addition of 10 mg of p-toluenesulfonic acid, the mixture was stirred at room temperature for 30 minutes. After completion of the reaction, 200 ml of ether was added to the mixture. The mixture was then washed with 3 portions of 100 ml of water and dried over anhydrous sodium sulfate. The solvent was evaporated to 2.8 g of the desired compound as an oil.

IR spectrum (liquid film) $v_{max}$cm$^{-1}$: 1740, 1375, 1240, 1200, 1020, 954.

11. ]α-Hydroxy-15-(2-tetrahydropyranyloxy)-20-isopropylideneprost-13(trans)-enoci acid (II)

In 90 ml of methanol was dissolved 3.0 g of methyl 9α-acetoxy-15-(2-tetrahydropyranyloxy)-20-isopropylideneprost-13(trans)enoate, and, after addition of 30 ml of 5% aqueous sodium hydroxide solution, the mixture was stirred at 40° C for 3 hour. After completion of the reaction, the mixture was diluted with ice-water, neutralized with 7% aqueous hydrochloric acid and extracted with ethyl acetate. The organic extract was washed with water and dried over anhydrous sodium sulfate. The solvent was evaporated under reduced pressure to leave 2.6 g of the desired compound as an oil.

IR spectrum (liquid film) $\nu_{max}$cm$^{-1}$: 3420, 2750, 1710, 1200, 1110, 1020, 970.

NMR spectrum (CDCl$_3$) δ ppm: 4.7 (1H, multiplet), 5.0 –0 5.5 (3H, multiplet), 6.0 (2H, multiplet).

Referential example 8

9α-Hydroxy-15-(2-tetrahydropyranyloxy)-20-isopropylidene-prost-5(cis), 13(trans)-dienoic acid (II)

1.

1α-Acetoxy-2α-(6-methoxycarbonyl-2-cis-hexenyl)-3β-formyl-cyclopentane (XXXV)

2.0 g of 1α-acetoxy-2α-(6-methoxycarbonyl-2-cis-hexenyl)-3β-hydroxymethyl-cyclopentane was reacted and treated in the same manner as in Referential example 7-(7) to give 1.95 g of the desired compound as an oil.

2. Methyl 9α-acetoxy-15-oxo-20-isopropylideneprost-5(cis), 13(trans)-dienoate (XXXVI)

1.95 g of 1α-acetoxy-2α(6-methoxycarbonyl-2-cis-hexenyl)-3α-formyl-cyclopentane was reacted and treated in the same manner as in Referential example 7-(8) to give 2.53 g of the desired compound as an oil.

IR spectrum (liquid film) $\nu_{max}$cm$^{-1}$: 1735, 1695, 1670, 1630, 1370, 1240, 1160, 1030.

NMR spectrum (CDCL$_3$) δ ppm: 2.02 (3H, singlet) 3.65 (3H, singlet), 5.0 – 5.5 (3H, multiplet), 6.10 (1H, doublet), 6.72 (1H, quarttet).

3. Methyl 9α-acetoxy-15-hydroxy-20-isopropylideneprost-5(cis), 13(trans)-dienoate (XXXVII)

2..58 g of methyl 9 α-acetoxy-15-oxo-20-isopropylideneprost-5(cis), 13(trans)dienoate was reacted and treated in the same manner as in Referential example 7-(9) to give 2.24 g of the desired compound as an oil.

IR spectrum (liquid film) $\nu_{max}$cm$^{-1}$: 3500, 1740, 1370, 1240, 1160, 1020, 965.

NMR spectrum (CDCl$_3$) δ ppm: 2.01 (3H, singlet), 3.67 (3H, singlet), 4.08 (1H, multiplet), 5.0 – 5.6 (5H, multiplet).

4. Methyl 9α-acetoxy-15-(2-tetrahydropyranyloxy)-20-isopropylideneprost-5(cis), 13(trans)-dienoate (XXXVIII)

2.20 g of methyl 9-acetoxy-15-hydroxy-20-isopropylideneprost-5(cis), 13(trans)-dienoate was reacted and treated in the same manner as in Referential example 7-(10) to give 2.90 g of the desired compound as an oil.

IR spectrum (liquid film) $\nu_{max}$cm$^{-1}$: 1740, 1370, 1240, 1200, 1015, 970.

5. 9α-Hydroxy-15-(2-tetrahydropyranyloxy)-20-isopropylideneprost-5(cis), 13(trans)-dienoic acid (II)

In 80 ml of methanol was dissolved 2.91 g of methyl 9α-acetoxy-15-(2-tetrahydropyranyloxy)-20-isopropylideneprost-5(cis), 13(trans)-dienoate, and after addition of 50 ml of 5% aqueous sodium hydroxide solution, the mixture was stirred at 40° C for 3 hours. After completion of the reaction, the reaction mixture was diluted with 200 ml of ice-water, neutralized with 7% aqueous hydrochloric acid and extracted with ethyl acetate. The extract was then washed with water and dried over anhydrous sodium sulfate. The solvent was evaporated under reduced pressure to leave 2.51 g of the desired compound as an oil.

IR spectrum (liquid film) $\nu_{max}$cm$^{-1}$: 3450, 3150, 2550, 1710, 1200, 1130, 1110, 1015, 965.

NMR spectrum (CDCl$_3$) δ ppm: 4.70 (1H, multiplet), 4.95 – 5.60 (5H, multiplet), 5.90 (2) H, multiplet).

What is claimed is:

1. Prostanoic acid derivative having the formula

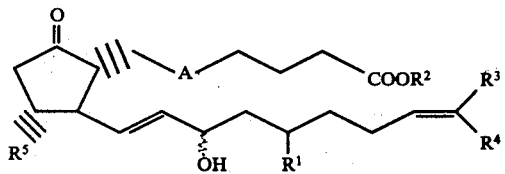

wherein A represents ethylene group or cis-vinylene group, R$^1$ and R$^2$ may be the same or different and each represents hydrogen atom or an alkyl group having 1 – 3 carbon atoms, R$^3$ and R$^4$ may be the same or different and each represents an alkyl group having 1 – 3 carbon atoms and R$^5$ represents hydroxy group and the pharamaceutically acceptable salts thereof.

2. 9-Oxo-11α,15α(or β)-dihydroxy-17β-methyl-20-isopropylideneprost-13(trans)-enoic acid.

3. Methyl 9-oxo-11α,15α(or β)-dihydroxy-17β-methyl-20-isopropylideneprost-13(trans)-enoate.

4. Potassium 9-oxo-11α, 15α(or β)-dihydroxy-17β-methyl-20-isopropylideneprost-13(trans)-enoate.

5. 9-Oxo-11α15α(or β)-dihydroxy-17β-methyl-20-isopropylideneprost-5(cis), 13(trans)-dienoic acid.

6. Methyl 9-oxo-11α,15α(or β)-dihydroxy-17β-methyl-20-isopropylideneprost-5(cis), 13(trans)-dienoate.

7. 9-Oxo-11α15α(or β)-dihydroxy-20-isopropylideneprost-13(trans)-enoic acid.

8. 9-Oxo-11α,15α(or β)-dihydroxy-20-isopropyideneprost-5(cis), 13(trans)-dienoic acid.

* * * * *

UNITED STATES PATENT AND TRADEMARK OFFICE
CERTIFICATE OF CORRECTION

PATENT NO. : 4,064,351
DATED : December 20, 1977
INVENTOR(S) : KIYOSHI SAKAI et al It is certified that error appears in the above-identified patent and that said Letters Patent are hereby corrected as shown below:

1) Column 3, lines 61 and 65: after "15α", delete "/".

2) Column 4, lines 1, 5 and 28: after "15α", delete "/".

3) Column 4, line 45: in formula "(II)", replace "  " with ---  --- (the double bond is wrong).

4) Column 8, line 20: before "alcohol", replace "as" with ---an---.

5) Column 9, line 46: after "protective group", delete the comma, and after "hydroxyl group", insert a comma.

6) Column 12, lines 26-27: rewrite "defind" as ---defined---.

7) Column 15, line 16: rewrite "moiesties" as ---moieties---.

8) Columns 15-16, after line 43: before the formula, insert: ---(3) Preparation of the starting compound having the above formula (II) wherein A is ethylene group and $R^{5'}$ is hydrogen atom---.

9) Column 17, line 66: replace "2-tetrahydrothioyranyl" with ---2-tetrahydrothiopyranyl---.

10) Column 19, line 65: in formula "(XXXIV)", replace "$(R^{20}O)_2$P-" with ---  ---.

UNITED STATES PATENT AND TRADEMARK OFFICE
CERTIFICATE OF CORRECTION

PATENT NO. : 4,064,351

DATED : December 20, 1977

INVENTOR(S) : KIYOSHI SAKAI et al

It is certified that error appears in the above-identified patent and that said Letters Patent are hereby corrected as shown below:

11) Columns 21-22, first line: before the formula, insert:
---(4) Preparation of the starting compound having the above formula (II) wherein A is cis-vinylene group and $R^{5'}$ is hydrogen atom---.

12) Column 21, formula "(XXXVIII)": replace
"" with ---  ---
(a double bond should be inserted).

13) Column 27, line 46: replace "-20° ∿ 10°C" with --- -20° ∿ -10°C ---.

14) Column 27, line 60: after "acetic", insert ---acid---.

15) Column 29, line 29: after "1015", insert a comma.

16) Column 30, line 23: replace "3.76" with ---376---.

17) Column 31, line 10: before "1α-(2-Tetra...", insert ---3. ---.

18) Column 32, line 29: rewrite "munutes" as ---minutes---.

19) Column 33, line 39: replace "9,69" with ---9.69---.

20) Column 33, line 46: rewrite "solutin" as ---solution---.

21) Column 34, line 38: replace "isopropyridene" with ---isopropylidene---.

UNITED STATES PATENT AND TRADEMARK OFFICE
CERTIFICATE OF CORRECTION

PATENT NO. : 4,064,351
DATED : December 20, 1977
INVENTOR(S) : KIYOSHI SAKAI et al It is certified that error appears in the above-identified patent and that said Letters Patent are hereby corrected as shown below:

22) Column 35, lines 59-60: rewrite "vigrously" as ---vigorously---.

23) Column 36, line 54: rewrite "synformly" as ---synformyl---.

24) Column 38, line 16: replace "(3·3·)" with ---(3·3·0)---.

25) Column 39, line 25: before "3-Hydroxy...", insert ---10. ---.

26) Column 40, line 8: rewrite "methly" as ---methyl---.

27) Column 45, line 47: rewrite "dischlormethane" as ---dichloromethane---.

28) Column 46, line 36: replace "evaporate" with ---evaporated---.

29) Column 46, line 63: rewrite "-enoci" as --- -enoic ---.

30) Column 46, line 62: replace "]α" with ---9α---.

31) Column 48, lines 50 (Claim 5) and 54 (Claim 7): rewrite "11α15α" as ---11α, 15α---.

UNITED STATES PATENT AND TRADEMARK OFFICE
CERTIFICATE OF CORRECTION

PATENT NO. : 4,064,351

DATED : December 20, 1977

INVENTOR(S) : KIYOSHI SAKAI et al

It is certified that error appears in the above-identified patent and that said Letters Patent are hereby corrected as shown below:

32) Column 48, line 56: rewrite "isopropyidene" as ---isopropylidene---.

Signed and Sealed this

Second Day of October 1979

[SEAL]

Attest:

RUTH C. MASON
Attesting Officer

LUTRELLE F. PARKER
Acting Commissioner of Patents and Trademarks